(12) United States Patent
Ducoux et al.

(10) Patent No.: US 6,642,233 B1
(45) Date of Patent: Nov. 4, 2003

(54) 1-PHENACYL-3-PHENYL-3-(PIPERIDYLETHYL)PIPERIDINE DERIVATIVES, PROCESS FOR THE PREPARATION THEREOF AND PHARMACEUTICAL COMPOSITIONS CONTAINING THEM

(75) Inventors: Jean-Philippe Ducoux, Combaillaux (FR); Xavier Emonds-Alt, Combaillaux (FR); Patrick Gueule, Teyran (FR); Vincenzo Proietto, Saint Georges D'Orques (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/913,106

(22) PCT Filed: Feb. 8, 2000

(86) PCT No.: PCT/FR00/00284
§ 371 (c)(1),
(2), (4) Date: Aug. 9, 2001

(87) PCT Pub. No.: WO00/47572
PCT Pub. Date: Aug. 17, 2000

(30) Foreign Application Priority Data

Feb. 10, 1999 (FR) .............................................. 99 01593
Apr. 7, 1999 (FR) .............................................. 99 04429

(51) Int. Cl.⁷ .................... A61K 31/535; A61K 31/445; C07D 211/14; C07D 413/14
(52) U.S. Cl. .................... 514/235.5; 514/326; 514/227; 514/316; 546/186; 546/189; 546/209; 544/106; 544/129
(58) Field of Search ................................. 546/186, 187, 546/189, 209; 544/106, 129; 540/596; 514/315, 316, 326, 227, 235.5

(56) References Cited

U.S. PATENT DOCUMENTS 5,340,822 A * 8/1994 Emonds-Alt et al. ....... 514/316
5,770,735 A  6/1998 Emonds-Alt et al.

FOREIGN PATENT DOCUMENTS

| EP | 0 512 901 | 11/1992 |
| EP | 0 714 891 | 6/1996 |
| WO | 96/06094 | 2/1996 |

* cited by examiner

Primary Examiner—Rita Desai
(74) Attorney, Agent, or Firm—Paul E. DuPont; Michael D. Alexander

(57) ABSTRACT

The invention relates to the compounds of formula:

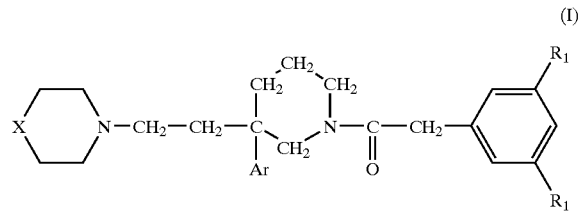

(I)

as well as to the salts thereof with inorganic or organic acids, to solvates thereof and/or to hydrates thereof, which have strong affinity and high selectivity for the human $NK_1$ receptors of substance P.

The invention also relates to the process for preparing them, to the intermediate compounds of formula (VII) which are useful for the preparation, to pharmaceutical compositions containing them and to their fuse for the manufacture of medicinal products intended for treating any pathology in which substance P and the human $NK_1$ receptors are involved.

15 Claims, No Drawings

1-PHENACYL-3-PHENYL-3-(PIPERIDYLETHYL)PIPERIDINE DERIVATIVES, PROCESS FOR THE PREPARATION THEREOF AND PHARMACEUTICAL COMPOSITIONS CONTAINING THEM

CROSS REFERENCE

This application is a 371 of PCT/FR00/00284 filed Feb. 8, 2000 and claims priority to France 99/01593 filed Feb. 10, 1999 & France 99/0662 filed Apr. 7, 1999.

The present invention relates to novel piperidine derivatives, to a process for preparing them and to pharmaceutical compositions containing them as active principle.

More particularly, the present invention relates to novel piperidine derivatives for therapeutic use in pathological phenomena involving the tachykinin system, such as, in a non-limiting manner: pain (L. Urban et al., TINS, 1994, 17, 432–438; L. Seguin et al., Pain, 1995, 61, 325–343; S. H. Buck, 1994, The Tachykinin Receptors, Humana Press, Totowa, N.J.), allergy and inflammation (S. H. Buck, 1994, The Tachykinin Receptors, Humana Press, Totowa, N.J.), gastrointestinal disorders (P. Holzer and U. Holzer-Petsche, Pharmacol. Ther., 1997, 73, 173–217 and 219–263), respiratory disorders (J. Mizrahi et al., Pharmacology, 1982, 25, 39–50; C. Advenier et al., Eur. Respir. J., 1997, 10, 1892–1906; C. Advenier and X. Emonds-Alt, Pulmonary Pharmacol., 1996, 9, 329–333), urinary disorders (S. H. Buck, 1994, The Tachykinin Receptors, Humana Press, Totowa, N.J.; C. A. Maggi, Progress in Neurobiology, 1995, 45, 1–98), neurological disorders and neuropsychiatric disorders (C. A. Maggi et al., J. Autonomic Pharmacol., 1993, 13, 23–93; M. Otsuka and K. Yoshioka, Physiol. Rev. 1993, 73, 229–308).

Many research studies have been carried out in recent years on tachykinins and their receptors. Tachykinins are distributed both in the central nervous system and in the peripheral nervous system. The tachykinin receptors have been recognized and are classified into three types: $NK_1$, $NK_2$ and $NK_3$. Substance P (SP) is the endogenous ligand of the $NK_1$ receptors, neurokinin A ($NK_A$) is that of the $NK_2$ receptors and neurokinin B ($NK_B$) is that of the $NK_3$ receptors.

The $NK_1$, $NK_2$ and $NK_3$ receptors have been demonstrated in various species.

A review by C. A. Maggi et al. (J. Autonomic Pharmacol., 1993, 13, 23–93) and a review by D. Regoli et al. (Pharmacol. Rev., 1994, 46, 551–599) discuss tachykinin receptors and their antagonists and present the pharmacological studies and the applications in human therapy.

Many patents and patent applications describe compounds that are active on tachykinin receptors. Thus, European patent application 0 512 901 relates to the compounds of formula:

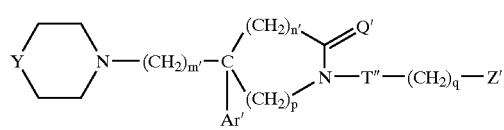

(A)

in which, in particular:

Q' represents an oxygen atom or two hydrogen atoms,
T'=—C(O)— or —CH$_2$—, and
Y, Ar', Z', m', n', p' and q have different values.

Patent application EP 0 714 891 relates to the compounds of formula:

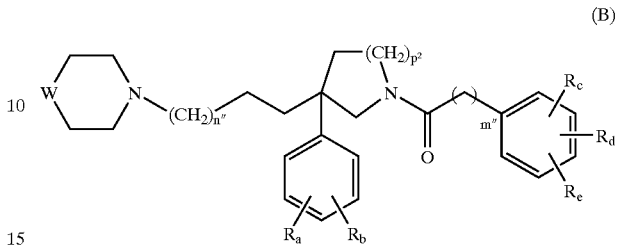

(B)

in which:
  p>> is 1, 2 or 3;
  m>> and n>> are independently 0 to 6;
  W, $R_a$, $R_b$, $R_c$, $R_d$ and $R_e$ have different values.

Novel compounds have now been found which have very strong affinity and great selectivity for the human $NK_1$ receptors of substance P and which are antagonists of the said receptors.

Furthermore, the compounds according to the present invention have good bioavailability when they are administered orally.

These compounds can be used to prepare medicinal products that are useful in the treatment of any pathology in which substance P and the $NK_1$ receptors are involved, in particular in the treatment of pathologies of the respiratory, gastrointestinal, urinary, immune, cardiovascular and central nervous systems as well as in the treatment of pain, migraine, inflammations, nausea and vomiting, and skin diseases.

Thus, according to one of its aspects, a subject of the present invention is compounds of formula:

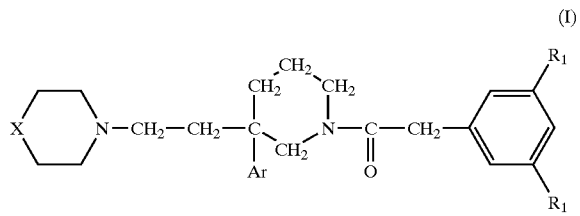

(I)

in which:
  Ar represents a phenyl monosubstituted or disubstituted with a halogen atom; a ($C_1$–$C_3$)alkyl;
  X represents a group

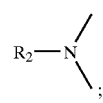

a group

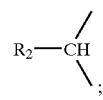

$R_1$ represents a chlorine atom, a bromine atom, a ($C_1$–$C_3$)alkyl or a trifluoromethyl;
  $R_2$ represents a group —$CR_3R_4CONR_5R_6$;
  $R_3$ and $R_4$ represent the same radical chosen from a methyl, an ethyl, an n-propyl or an n-butyl;

or alternatively $R_3$ and $R_4$, together with the carbon atom to which they are attached, constitute a $(C_3-C_6)$ cycloalkyl;

$R_5$ and $R_6$ each independently represent a hydrogen; a $(C_1-C_3)$alkyl;

or alternatively $R_5$ and $R_6$, together with the nitrogen atom to which they are attached, constitute a heterocyclic radical chosen from 1-azetidinyl, 1-pyrrolidinyl, 1-piperidyl, 4-morpholinyl, 4-thiomorpholinyl or perhydro-1-azepinyl; as well as the possible salts thereof with inorganic or organic acids, and the solvates and/or hydrates thereof.

The compounds of formula (I) according to the invention comprise both optically pure isomers and mixtures thereof in any proportion.

Salts of the compounds of formula (I) can be formed. These salts comprise both those with inorganic or organic acids which allow a suitable separation or crystallization of the compounds of formula (I), such as picric acid or oxalic acid or an optically active acid, for example a mandelic or camphorsulphonic acid, and those which form pharmaceutically acceptable salts, such as the hydrochloride, hydrobromide, sulphate, hydrogen sulphate, dihydrogen phosphate, methanesulphonate, methyl sulphate, oxalate, maleate, fumarate, succinate, 2-naphthalenesulphonate, gluconate, citrate, benzenesulphonate or para-toluenesulphonate.

The term <<halogen>> means a chlorine, bromine, fluorine or iodine atom.

In the present description, the alkyl groups are straight or branched.

According to the present invention, the preferred compounds are those of formula:

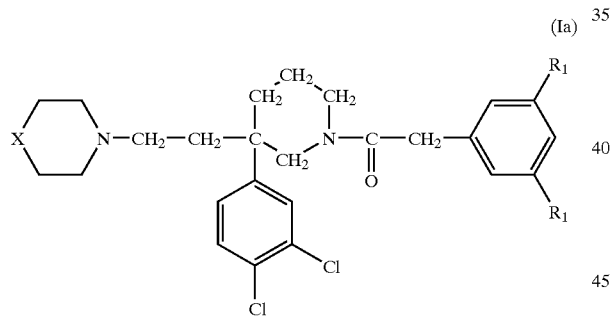

(Ia)

in which X and $R_1$ are as defined for a compound of formula (I), as well as the salts thereof with inorganic or organic acids, and the solvates and/or hydrates thereof.

According to the present invention, the preferred compounds of formula (I) are those in which Ar represents a 3,4-dichlorophenyl or a 3,4-dimethylphenyl.

According to the present invention, the preferred compounds of formula (I) are those in which the substituents $R_1$ represent a chlorine atom, a methyl, an ethyl or a trifluoromethyl.

According to the present invention, the preferred compounds of formula (I) are those in which X represents a group

in which $R_2$ represents a group —$CR_3R_4CONR_5R_6$.

Particularly, the preferred compounds are those in which $R_3$ and $R_4$ each represent a methyl or alternatively, together with the carbon atom to which they are attached, constitute a cyclohexyl. Particularly, the compounds which are also preferred are those in which $R_5$ and $R_6$ each represent hydrogen or a methyl.

According to the present invention, the preferred compounds of formula (I) are those in which X represents a group

in which $R_2$ represents a group —$CR_3R_4CONR_5R_6$.

Particularly, the preferred compounds are those in which $R_3$ and $R_4$ each represent a methyl or alternatively, together with the carbon atom to which they are attached, constitute a cyclopropyl or a cyclohexyl. Particularly, the compounds which are also preferred are those in which $R_5$ and $R_6$ each represent hydrogen or a methyl.

According to the present invention, the compounds which are preferred are those of formula:

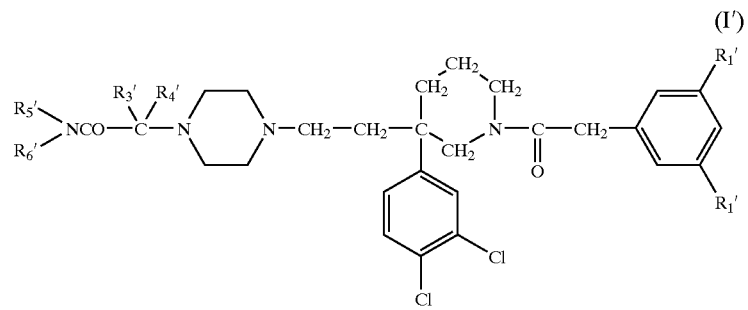

(I')

in which:
  R'₁ represents a chlorine atom, a methyl, an ethyl or a trifluoromethyl;
  R'₃ and R'₄ each represent a methyl or alternatively, together with the carbon atom to which they are attached, constitute a cyclohexyl;
  R'₅ and R'₆ each represent hydrogen or a methyl; as well as the salts thereof with inorganic or organic acids, and the solvates and/or hydrates thereof.

According to the present invention, the preferred compounds are those of formula:

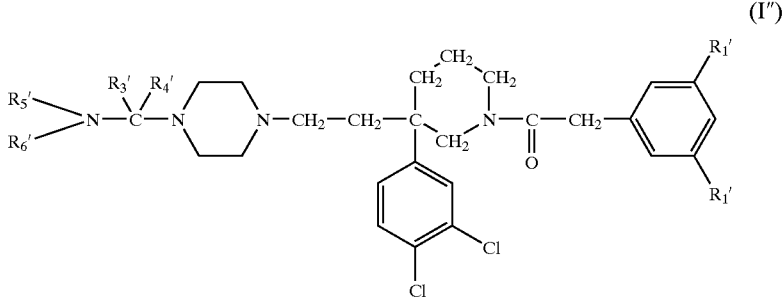

(I'')

in which:
  R'₁ represents a chlorine atom, a methyl, an ethyl or a trifluoromethyl;
  R'₃ and R'₄ each represent a methyl or alternatively, together with the carbon atom to which they are attached, constitute a cyclohexyl or cyclopropyl;
  R'₅ and R'₆ each represent hydrogen or a methyl; as well as the salts thereof with inorganic or organic acids, and the solvates and/or hydrates thereof.

According to the present invention, the preferred compounds are those of formulae (I), (I') and (I>>) in optically pure form.

The following compounds:

3-[2-[4-(1-carbamoyl-1-methylethyl)-1-piperidyl]ethyl]-3-(3,4-dichlorophenyl)-1-[2-(3,5-dimethylphenyl)acetyl]piperidine, (−) isomer;
3-[2-[4-(1-carbamoyl-1-methylethyl)-1-piperazinyl]ethyl]-3-(3,4-dichlorophenyl)-1-[2-(3,5-dimethylphenyl)acetyl]piperidine, (−) isomer;
3-[2-[4-(1-N,N-dimethylcarbamoyl-1-methylethyl)-1-piperazinyl]ethyl]-3-(3,4-dichlorophenyl)-1-[2-(3,5-dimethylphenyl)acetyl]piperidine, (−) isomer;
3-[2-[4-(1-carbamoyl-1-methylethyl)-1-piperidyl]ethyl]-3-(3,4-dichlorophenyl)-1-[2-(3,5-dichlorophenyl)acetyl]piperidine, (−) isomer;
3-[2-[4-(1-carbamoyl-1-methylethyl)-1-piperidyl]ethyl]-3-(3,4-dichlorophenyl)-1-[2-(3,5-bis(trifluoromethyl)phenyl]acetyl]piperidine, (+) isomer;
3-[2-[4-(1-carbamoylcyclohexyl)-1-piperidyl]ethyl]-3-(3,4-dichlorophenyl)-1-[2-(3,5-dimethylphenyl)acetyl]piperidine, (−) isomer;
3-[2-[4-(1-carbamoylcyclohexyl)-1-piperazinyl]ethyl]-3-(3,4-dichlorophenyl)-1-[2-(3,5-dimethylphenyl)acetyl]piperidine, (−) isomer;
3-[2-[4-(1-carbamoylcyclohexyl)piperidin-1-yl]ethyl]-3-(3,4-dichlorophenyl)-1-[2-(3,5-dichlorophenyl)acetyl]piperidine, (−) isomer;
3-[2-[4-(1-carbamoyl-1-methylethyl)piperazin-1-yl]ethyl]-3-(3,4-dichlorophenyl)-1-[2-(3,5-dichlorophenyl)acetyl]piperidine, (+) isomer;
3-[2-[4-(1-N,N-dimethylcarbamoyl-1-methylethyl)-1-piperazinyl]ethyl]-3-(3,4-dichlorophenyl)-1-[2-(3,5-dichlorophenyl)acetyl]piperidine, (+) isomer;
3-[2-[4-(1-carbamoylcyclohexyl)-1-piperazinyl]ethyl]-3-(3,4-dichlorophenyl)-1-[2-(3,5-dichlorophenyl)acetyl]piperidine, (+) isomer;
3-[2-[4-(1-carbamoylcyclohexyl)-1-piperidyl]ethyl]-3-(3,4-dichlorophenyl)-1-[2-[3,5-bis(trifluoromethyl)phenyl]acetyl]piperidine, (+) isomer;
3-[2-[4-(1-carbamoylcyclohexyl)-1-piperazinyl]ethyl]-3-(3,4-dichlorophenyl)-1-[2-[3,5-bis(trifluoromethyl)phenyl]acetyl]piperidine, (+) isomer;
3-[2-[4-(1-N,N-dimethylcarbamoyl-1-methylethyl)-1-piperidyl]ethyl]-3-(3,4-dichlorophenyl)-1-[2-(3,5-dimethylphenyl)acetyl]piperidine, (−) isomer;
3-[2-[4-(1-carbamoyl-1-methylethyl)-1-piperidyl]ethyl]-3-(3,4-dichlorophenyl)-1-[2-(3,5-diethylphenyl)acetyl]piperidine, (−) isomer;
3-[2-[4-(1-carbamoylcyclopropyl)-1-piperidyl]ethyl]-3-(3,4-dichlorophenyl)-1-[2-(3,5-dimethylphenyl)acetyl]piperidine, (−) isomer;
3-[2-[4-(1-carbamoylcyclopropyl)-1-piperidyl]ethyl]-3-(3,4-dichlorophenyl)-1-[2-[3,5-bis(trifluoromethyl)phenyl]acetyl]piperidine, (+) isomer;
3-[2-[4-(1-carbamoylcyclopropyl)-1-piperidyl]ethyl]-3-(3,4-dichlorophenyl)-1-[2-(3,5-dichlorophenyl)acetyl]piperidine, (+) isomer;
3-[2-[4-(1-carbamoyl-1-methylethyl)-1-piperazinyl]ethyl]-3-(3,4-dichlorophenyl)-1-[2-(3,5-diethylphenyl)acetyl]piperidine, (−) isomer;
3-[2-[4-(1-carbamoyl-1-methylethyl)-1-piperidyl]ethyl]-3-(3,4-dimethylphenyl)-1-[2-(3,5-dichlorophenyl)acetyl]piperidine;
3-[2-[4-(1-carbamoyl-1-methylethyl)-1-piperazinyl]ethyl]-3-(3,4-dimethylphenyl)-1-[2-(3,5-dichlorophenyl)acetyl]piperidine;

as well as the salts thereof, and the solvates and/or hydrates thereof, are more particularly preferred.

According to another of its aspects, the present invention relates to a process for preparing compounds of formula (I), the salts thereof and the solvates and/or hydrates thereof, characterized in that:

1a) a compound of formula:

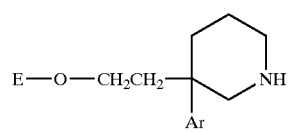

(II)

in which Ar is as defined for a compound of formula (I) and E represents hydrogen or an O-protecting group, is treated with a functional derivative of an acid of formula:

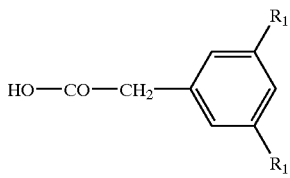
(III)

in which R$_1$ is as defined for a compound of formula (I), to give a compound of formula:

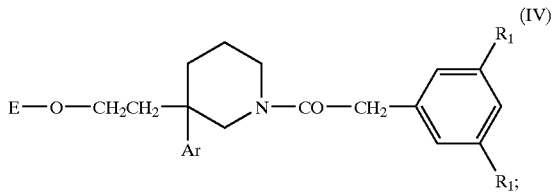
(IV)

2a) optionally, when E represents a protecting group, it is removed by the action of an acid or a base, to

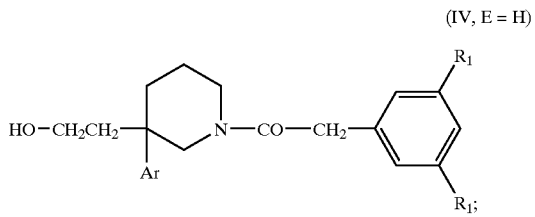
(IV, E = H)

give the alcohol of formula:
3a) the alcohol obtained in step 1a) or in step 2a) of formula (IV, E=H) is treated with a compound of formula:

$$Y\text{—}SO_2\text{—}Cl \quad (V)$$

in which Y represents a methyl, phenyl, tolyl or trifluoromethyl group, to give a compound of formula:

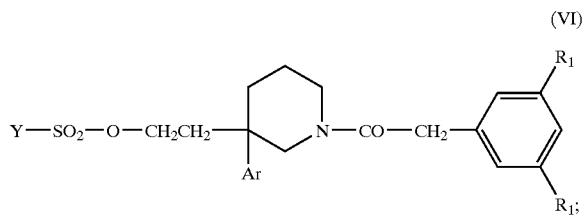
(VI)

4a) the compound of formula (VI) is reacted with a compound of formula:

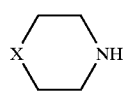
(VII)

in which X is as defined for a compound of formula (I);
5a) and, optionally, the compound thus obtained is converted into one of the salts thereof with an inorganic or organic acid.

When E represents an O-protecting group, this group is chosen from conventional O-protecting groups that are well known to those skilled in the art, such as, for example, 2-tetrahydropyranyl, benzoyl or a (C$_1$–C$_4$)alkylcarbonyl.

In step 1a), the functional derivative of the acid (III) which is used is the acid itself or alternatively one of the functional derivatives which react with amines, for example an anhydride, a mixed anhydride, acid chloride or an activated ester, such as the para-nitrophenyl ester.

When the acid of formula (III) itself is used, the process is performed in the presence of a coupling agent used in peptide chemistry, such as 1,3-dicyclohexylcarbodiimide or benzotriazole-1-yloxytris(dimethylamino)phosphonium hexafluorophosphate in the presence of a base such as triethylamine or N,N-diisopropylethylamine, in an inert solvent such as dichloromethane or N,N-dimethylformamide, at a temperature of between 0° C. and room temperature.

When an acid chloride is used, the reaction is carried out in an inert solvent such as dichloromethane or benzene, in the presence of a base such as triethylamine or N-methylmorpholine and at a temperature of between −60° C. and room temperature.

The compound of formula (IV) thus obtained is optionally deprotected in step 2a) according to the methods that are known to those skilled in the art. For example, when E represents a 2-tetrahydropyranyl group, the deprotection is carried out by acidic hydrolysis using hydrochloric acid in a solvent such as ether, methanol or a mixture of these solvents, or using pyridinium p-toluenesulphonate in a solvent such as methanol, or alternatively using an Amberlyst® resin in a solvent such as methanol. The reaction is carried out at a temperature between room temperature and the reflux temperature of the solvent. When E represents a benzoyl group or a (C$_1$–C$_4$)alkylcarbonyl group, the deprotection is carried out by hydrolysis in alkaline medium using, for example, an alkali metal hydroxide such as sodium hydroxide, potassium hydroxide or lithium hydroxide, in an inert solvent such as water, methanol, ethanol, dioxane or a mixture of these solvents, at a temperature of between 0° C. and the reflux temperature of the solvent.

In step 3a), the reaction of the alcohol of formula (IV, E=H) with a sulphonyl chloride of formula (V) is carried out in the presence of a base such as triethylamine, pyridine, N,N-diisopropylethylamine or N-methylmorpholine, in an inert solvent such as dichloromethane, benzene or toluene, at a temperature of between −20° C. and the reflux temperature of the solvent.

The compound of formula (VI) thus obtained is reacted in step 4a) with a compound of formula (VII). The reaction is carried out in an inert solvent such as N,N-dimethylformamide, acetonitrile, methylene chloride, toluene or isopropanol and in the presence or absence of a base. When a base is used, it is chosen from organic bases such as triethylamine, N,N-diisopropylethylamine or N-methylmorpholine and from alkali metal carbonates or bicarbonates such as potassium carbonate, sodium carbonate or sodium bicarbonate. In the absence of a base, the reaction is carried out using an excess of the compound of formula (VII) and in the presence of an alkali metal iodide such as potassium iodide or sodium iodide. The reaction is carried out at a temperature between room temperature and 100° C.

According to one variant of the process:
1b) it is performed as in step 1a) and optionally as in step 2a);
2b) the compound of formula (IV, E=H) thus obtained is oxidized in order to prepare a compound of formula:

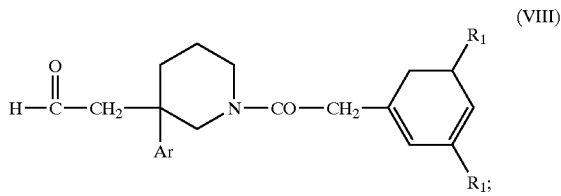
(VIII)

3b) the compound of formula (VIII) is reacted with a compound of formula (VII) as defined above, in the presence of an acid, followed by reduction of the intermediate iminium salt formed, by means of a reducing agent;

4b) and, optionally, the compound thus obtained is converted into one of the salts thereof with an inorganic or organic acid.

According to the variant of the process, in step 2b), an alcohol of formula (IV, E=H) is subjected to an oxidation, to give an aldehyde of formula (VIII). The oxidation reaction is carried out using, for example, oxalyl chloride, dimethyl sulphoxide and triethylamine in a solvent such as dichloromethane and at a temperature of between −78° C. and room temperature.

Next, in step 3b), the compound of formula (VII) is reacted with an aldehyde of formula (VIII) in the presence of an acid such as acetic acid, in an inert solvent such as methanol or dichloromethane, to form in situ an intermediate imine which is reduced chemically using, for example, sodium cyanoborohydride or sodium triacetoxyborohydride, or reduced catalytically using hydrogen and a catalyst such as palladium-on-charcoal or Raney® nickel.

Finally, the compounds of formula (I) according to the invention are obtained.

The compounds of formula (I) thus obtained are isolated in the form of the free base or in the form of a salt, according to the conventional techniques.

When the compounds of formula (I) are obtained in the form of the free base, the salification is carried out by treatment with the acid chosen in an organic solvent. Treatment of the free base, dissolved, for example, in an ether such as diethyl ether or in an alcohol such as 2-propanol or in acetone or in dichloromethane, or in ethyl acetate, with a solution of the acid chosen in one of the abovementioned solvents, gives the corresponding salt which is isolated according to the conventional techniques.

Thus, for example, the hydrochloride, the hydrobromide, the sulphate, the hydrogen sulphate, the dihydrogen phosphate, the methanesulphonate, the methyl sulphate, the oxalate, the maleate, the succinate, the fumarate, the 2-naphthalenesulphonate, the benzenesulphonate, the para-toluenesulphonate or the gluconate is prepared.

At the end of the reaction, the compounds of formula (I) can be isolated in the form of one of the salts thereof, for example the hydrochloride or the oxalate; in this case, if necessary, the free base can be prepared by neutralizing the said salt with an inorganic or organic base, such as sodium hydroxide or triethylamine or with an alkali metal carbonate or bicarbonate, such as sodium or potassium carbonate or bicarbonate.

The compounds of formula (II) are prepared by known methods, in particular those described in patent applications EP-A-0 512 901, EP-A-0 591 040 or EP-A-0 714 891.

The compounds of formula (III) are commercially available or are prepared according to known methods.

Thus, for example, the compounds of formula (III) are prepared according to SCHEME 1 below.

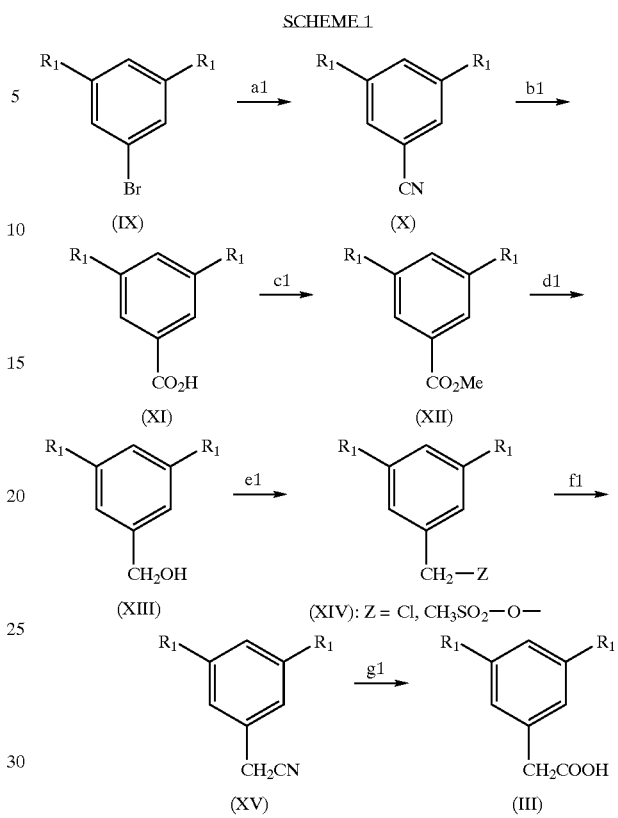

Steps a1 and b1 of SCHEME 1 are carried out according to the methods described in J. Am. Chem. Soc., 1941, 63, 3280–3282.

In step c1, an ester of formula (XII) is prepared from an acid of formula (XI) according to the methods known to those skilled in the art.

The ester (XII) thus obtained is reduced in step d1 to the alcohol of formula (XIII) according to the methods known to those skilled in the art.

Steps e1 and f1 are carried out according to the methods described in J. Med. Chem., 1973, 16, 684–687.

The phenylacetonitrile derivatives of formula (XV) thus obtained are hydrolysed in step g1 into compounds of formula (III) according to the methods described in J. Org. Chem., 1968, 33, 4288 or in EP-A-0 714 891.

The bromo derivatives of formula (IX) are known or are prepared according to known methods, such as those described in J. Org. Chem., 1971, 36(1), 193–196, or in J. Am. Chem. Soc., 1941, 63, 3280–3282.

The compounds of formula (VII) in which X represents a group

in which $R_2$ represents a group —$CR_3R_4CONR_5R_6$ are prepared according to SCHEME 2 below:

SCHEME 2

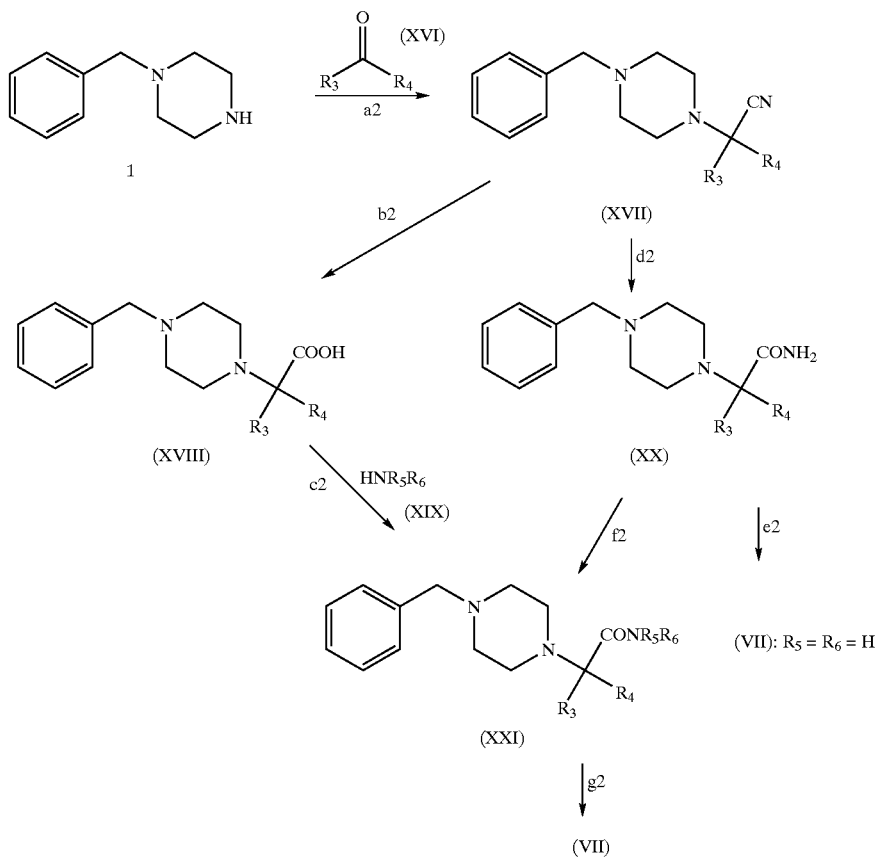

In step a2 of SCHEME 2, compound 1 is reacted with a ketone of formula (XVI), in the presence of 2-hydroxyisobutyronitrile, according to the method described in Eur. J. Med. Chem., 1990, 25, 609–615.

The nitrile derivative of formula (XVII) thus obtained is hydrolysed in step b2 according to the methods known to those skilled in the art, to give an acid derivative of formula (XVIII).

The acid (XVIII) is reacted in step c2 with an amine of formula (XIX) according to the conventional methods of peptide coupling, to give the derivative (XXI).

Alternatively, in step d2, the nitrile derivative of formula (XVII) is hydrolysed according to the known methods, to give the carboxamide derivative of formula (XX), which is optionally deprotected in step e2, according to the conventional methods, to give compound (VII) in which $R_5=R_6=H$.

In step f2, by reacting the compound of formula (XX), in the presence of a strong base, respectively, with a $(C_1-C_3)$ alkyl halide, or successively with two $(C_1-C_3)$alkyl halides, or with a dihalide of formula Hal—$R_5$—$R_6$—Hal, according to the conventional alkylation methods, a compound of formula (XXI) is prepared in which, respectively, $R_5$ represents a $(C_1-C_3)$alkyl and $R_6$=H, or $R_5$ and $R_6$ each independently represent a $(C_1-C_3)$alkyl, or $R_5$ and $R_6$, together with the nitrogen atom to which they are attached, constitute a heterocycle.

The compound (XXI) thus obtained is deprotected in step g2, according to the known methods, to give the expected compound (VII).

The compounds of formula (VII) in which X represents a group

in which $R_2$ represents a group —$CR_3R_4CONR_5R_6$ are prepared according to SCHEME 3 below.

SCHEME 3

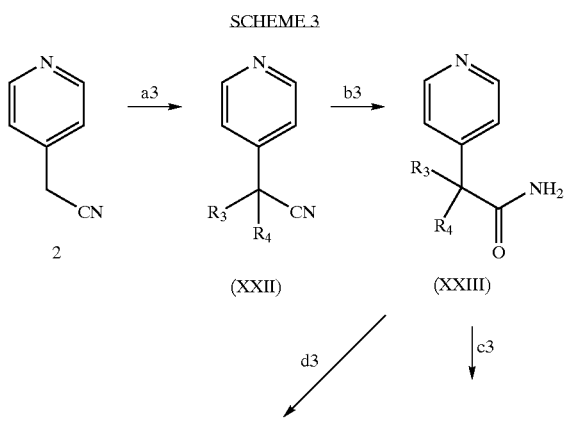

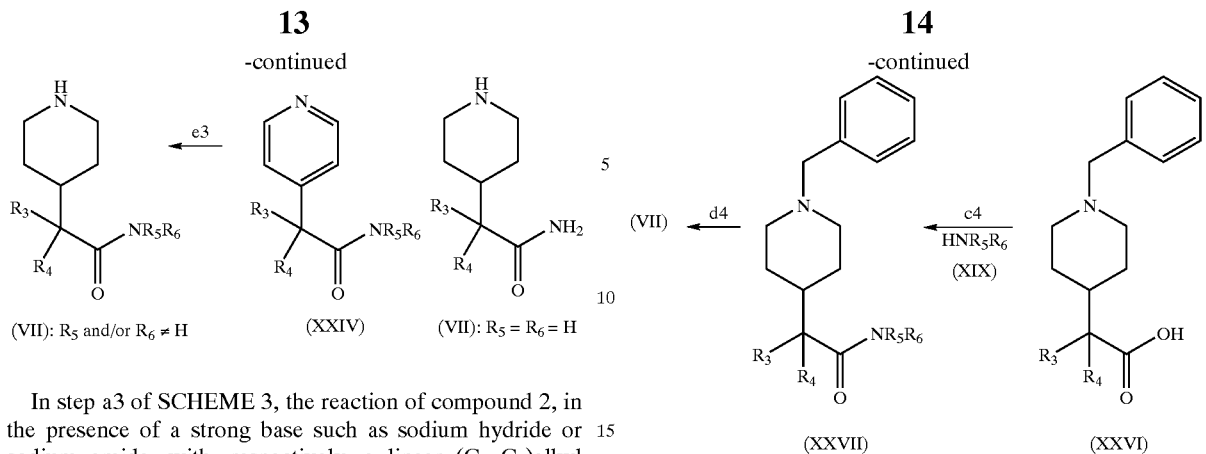

In step a3 of SCHEME 3, the reaction of compound 2, in the presence of a strong base such as sodium hydride or sodium amide, with, respectively, a linear $(C_1–C_4)$alkyl halide, or with a dihalide of formula $Hal(CH_2)_m$-Hal in which m=2 to 5 and Hal represents a halogen atom, in an inert solvent such as N,N-dimethylformamide or dichloromethane and at a temperature of between 0° C. and room temperature, according to the conventional alkylation methods, gives the compound of formula (XXII) in which, respectively, $R_3$ and $R_4$ each represent a linear $(C_1–C_4)$alkyl or, together with the carbon atom to which they are attached, constitute a $(C_3–C_6)$cycloalkyl.

The nitrile derivative (XXII) thus obtained is hydrolysed in step b3, according to the methods known to those skilled in the art, to give the carboxamide derivative (XXIII). Optionally, in step c3, the pyridine ring is hydrogenated, in the presence of a catalyst such as platinum oxide, according to the known methods, to give a compound of formula (VII) in which $R_5$ and $R_6$=H.

In step d5, alkylation reaction, according to the conventional methods described previously, of the compound of formula (XXIII), followed by reduction, by means of conventional catalytic hydrogenation, of the compound (XXIV) thus obtained gives a compound of formula (VII) in which $R_5$ and/or $R_6 \neq H$.

The compounds of formula (VII) in which X represents a group

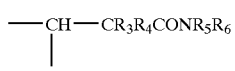

can also be obtained according to SCHEME 4 below.

SCHEME 4

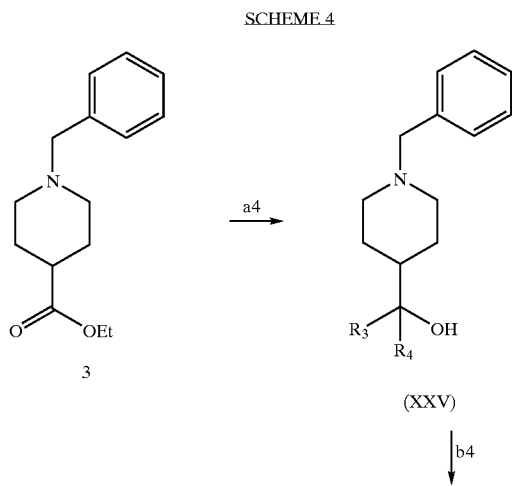

In step a4 of SCHEME 4, reaction of compound 3 with a suitable organolithium or organomagnesium derivative such as, for example, methyllithium, ethylmagnesium chloride, propylmagnesium chloride or pentane-1,5-di(magnesium chloride), according to the methods described in EP-A-0 625 509, gives the alcohol of formula (XXV).

The alcohol (XXV) thus obtained is oxidized in step b4 into the acid of formula (XXVI) according to the method described in Helvetica Chimica Acta, 1972, 55 (7), 2439.

The acid (XXVI) is reacted in step c4 with an amine of formula (XIX) according to the conventional methods of peptide coupling, to give compound (XXVII).

Compound (XXVII) is deprotected in step d4, according to the known methods, to give the expected compound (VII).

Compound 3 is prepared by reacting ethyl isonipecotate with benzylbromide, in the presence of a base, according to the conventional alkylation methods.

The compounds of formula (VII) are novel and form part of the invention.

Thus, according to another of its aspects, a subject of the invention is a compound of formula:

in which:

X represents a group

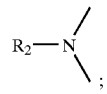

a group

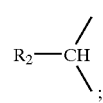

$R_2$ represents a group $—CR_3R_4CONR_5R_6$;

$R_3$ and $R_4$ represent the same radical chosen from a methyl, an ethyl, an n-propyl or an n-butyl;

or $R_3$ and $R_4$, together with the carbon atom to which they are attached, constitute a $(C_3–C_6)$cycloalkyl;

$R_5$ and $R_6$ each independently represent a hydrogen; a $(C_1–C_3)$alkyl;

or alternatively $R_5$ and $R_6$, together with the nitrogen atom to which they are attached, constitute a heterocyclic radical chosen from 1-azetidinyl, 1-pyrrolidinyl, 1-piperidyl, 4-morpholinyl, 4-thiomorpholinyl or perhydro-1-azepinyl; and the salts thereof with inorganic or organic acids.

The resolution of the racemic mixtures of the compounds of formula (I) makes it possible to isolate the enantiomers of formula (I*)

![structure]

in which:

<<*>> means that the carbon atom thus labelled has the determined (S) or (R) absolute configuration;

X, Ar and $R_1$ are as defined for a compound of formula (I);

as well as the possible salts thereof with inorganic or organic acids, and the solvates and/or hydrates thereof.

However, it is preferable to carry out the resolution of the racemic mixtures from the intermediate compound of formula (II, E=H), which is useful for preparing the compound of formula (I) as described in the patent applications: EP-A-0 512 901, EP-A-0 612 716 and EP-A-0 591 040.

According to another of its aspects, the present invention relates to a stereospecific process for preparing the compounds of formula (I) having the (S) configuration, the salts thereof and the solvates and/or hydrates thereof, characterized in that: 1d) the (S) isomer of a compound of formula:

(II*, E=H)

![structure]

in which Ar is as defined for a compound of formula (I), is treated with a functional derivative of the acid of formula:

(III)

![structure]

in which $R_1$ is as defined for a compound of formula (I), to give a compound of formula:

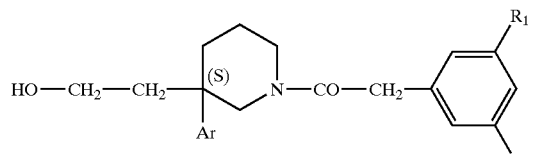
(IV*, E=H)

2d) the compound of formula (IV*) is oxidized to give a compound of formula:

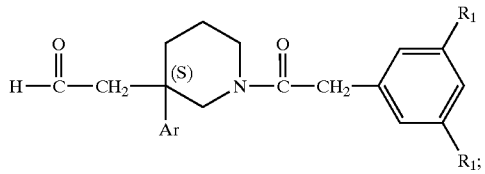
(VIII*)

3d) the compound of formula (VIII*) is reacted with a compound of formula:

(VII)

in which X is as defined for a compound of formula (I), in the presence of an acid, followed by reduction of the intermediate iminium salt formed by means of a reducing agent;

4d) and, optionally, the compound thus obtained is converted into one of the salts thereof with an inorganic or organic acid.

The compounds of formula (I) above also comprise those in which one or more hydrogen or carbon atoms have been replaced with their radioactive isotope, for example tritium or carbon-14. Such labelled compounds are useful in research studies, of metabolism or of pharmacokinetics, in biochemical tests as receptor ligands.

The compounds according to the invention underwent biochemical tests.

The affinity of the compounds for the tachykinin receptors was evaluated in vitro by means of several biochemical tests using radio ligands:

1) The binding of [$^{125}$I] BH-SP (substance P labelled with iodine-125 using the Bolton-Hunter reagent) to the $NK_1$ receptors of human lymphoblast cells (D. G. Payan et al., J. Immunol., 1984, 133, 3260–3265).
2) The binding of [$^{125}$I] His-$NK_A$ to human $NK_2$ cloned receptors expressed by CHO cells (Y. Takeda et al., J. Neurochem., 1992, 59, 740–745).
3) The binding of [$^{125}$I] His [MePhe$^7$] $NK_B$ to the $NK_3$ receptors of rat cerebral cortex, of guinea pig cerebral cortex and of gerbil cerebral cortex as well as to the human $NK_3$ cloned receptors expressed by CHO cells (Buell et al., FEBS Letters, 1992, 299, 90–95).

The tests were carried out according to X. Emonds-Alt et al., (Eur. J. Pharmacol., 1993, 250, 403–413; Life Sci., 1995, 56, PL 27–32).

The compounds according to the invention strongly inhibit the binding of substance P to the $NK_1$ receptors of human IM9 lymphoblast cells. The inhibition constant Ki for the human lymphoblast cell receptors is of the order of $10^{-11}$M.

The inhibition constants Ki for the human $NK_2$ cloned receptors are of the order of $10^{-8}$M and the inhibition constants Ki for the human $NK_3$ cloned receptors are greater than $10^{-7}$M.

The compounds of formula (I) are powerful and selective antagonists of substance P for the human $NK_1$ receptors.

Thus, the compounds of formula (I) were also evaluated in vivo on animal models.

In guinea pig striatum, the local application of an agonist which is specific for the $NK_1$ receptors, for example [$Sar^9$, $Met(O_2)^{11}$]substance P, increases the release of acetylcholine. This release is inhibited by oral or intraperitoneal administration of the compounds according to the present invention. This test was adapted from the method described by R. Steinberg et al., J. Neurochemistry, 1995, 65, 2543–2548.

These results show that the compounds of formula (I) are active orally, that they cross the blood-brain barrier and that they are capable of blocking the action specific to the $NK_1$ receptors in the central nervous system.

The compounds of formula (I) were evaluated in the test of bronchoconstriction in guinea pigs, according to the method described by X. Emonds-Alt et al., European Journal of Pharmacology, 1993, 250, 403–413. The compounds of formula (I) administered intravenously strongly antagonize the broncho-constriction induced by intravenous administration of septide to guinea pigs under these experimental conditions.

The in vivo pharmacological activity of the compounds of formula (I) was also evaluated in the model of hypotension in dogs, according to the method described by X. Emonds-Alt et al., Eur. J. Pharmacol., 1993, 250, 403–413. The compounds of formula (I) administered intravenously strongly inhibit the hypotension induced by intravenous administration of [$Sar^9$, $Met(O_2)^{11}$]substance P in anaesthetized dogs under these experimental conditions.

These results show that the compounds of formula (I) block the action specific to the $NK_1$ receptors in the peripheral nervous system.

The compounds of the present invention are, in particular, active principles of pharmaceutical compositions, whose toxicity is compatible with their use as medicinal products.

The compounds of formula (I) above can be used at daily doses of from 0.01 to 100 mg per kilo of body weight of the mammal to be treated, preferably at daily doses of from 0.1 to 50 mg/kg. In human beings, the dose can preferably range from 0.1 to 4000 mg per day, more particularly from 0.5 to 1000 mg depending on the age of the individual to be treated or the type of treatment: prophylatic or curative.

For their use as medicinal products, the compounds of formula (I) are generally administered in dosage units. The said dosage units are preferably formulated in pharmaceutical compositions in which the active principle is mixed with one or more pharmaceutical excipients.

Thus, according to another of its aspects, the present invention relates to pharmaceutical compositions containing, as active principle, a compound of formula (I) or one of the pharmaceutically acceptable salts, solvates and/or hydrates thereof.

In the pharmaceutical compositions of the present invention for oral, sublingual, inhaled, subcutaneous, intramuscular, intravenous, transdermal, local or rectal administration, the active principles can be administered in unit forms of administration, mixed with conventional pharmaceutical supports, to animals and to human beings. The appropriate unit forms of administration comprise oral-route forms such as tablets, gel capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition is prepared in the form of tablets or gel capsules, a mixture of pharmaceutical excipients which can be composed of diluents such as, for example, lactose, microcrystalline cellulose, starch, dicalcium phosphate, binders such as, for example, polyvinylpyrrolidone, hydroxypropylmethylcellulose, crumbling agents such as crosslinked polyvinylpyrrolidone, crosslinked carboxymethyl-cellulose, flow agents such as silica or talc, and lubricants such as magnesium stearate, stearic acid, glyceryl tribehenate or sodium stearyl fumarate, is added to the micronized or non-micronized active principle.

Wetting agents or surfactants such as sodium lauryl sulphate, polysorbate 80 or poloxamer 188 can be added to the formulation.

The tablets can be prepared by various techniques: direct tabletting, dry granulation, wet granulation, hot-melt.

The tablets may be naked or sugar-coated (for example with sucrose) or coated with various polymers or other suitable materials.

The tablets can have a flash, delayed or sustained release by preparing polymer matrices or by using specific filming polymers.

The gel capsules can be soft or hard, and coated with film or otherwise, so as to have flash, sustained or delayed activity (for example via an enteric form).

They can contain not only a solid formulation formulated as above for the tablets, but also liquid or semi-solid formulations.

A preparation in the form of a syrup or elixir can contain the active principle together with a sweetener, preferably a calorie-free sweetener, methyl paraben and propyl paraben as antiseptic agent, as well as a flavouring agent and a suitable colorant.

The water-dispersible powders or granules can contain the active principle as a mixture with dispersants, wetting agents or suspending agents, such as polyvinylpyrrolidone, as well as with sweeteners or flavour enhancers.

For rectal administration, use is made of suppositories which are prepared with binders that melt at the rectal temperature, for example cocoa butter or polyethylene glycols.

Aqueous suspensions, isotonic saline solutions or sterile, injectable solutions which contain pharmacologically compatible dispersants and/or solubilizing agents, for example propylene glycol, are used for parenteral, intranasal or intraocular administration.

Thus, in order to prepare an aqueous solution which can be injected intravenously, a co-solvent such as, for example, an alcohol such as ethanol or a glycol such as polyethylene glycol or propylene glycol, and a hydrophilic surfactant such as polysorbate 80 or poloxamer 188 can be used. To prepare an injectable oily solution for intramuscular administration, the active principle can be dissolved with a triglyceride or a glycerol ester.

Creams, ointments, gels, eye drops and sprays can be used for local administration.

Patches in multilaminar or reservoir form in which the active principle can be in alcoholic solution, and sprays can be used for transdermal administration.

An aerosol containing, for example, sorbitan trioleate or oleic acid as well as trichlorofluoromethane, dichlorofluoromethane, dichlorotetrafluoroethane, freon substitutes or any other biologically compatible propellent gas is used for administration by inhalation; a system containing the active principle alone or combined with an excipient, in powder form, can also be used.

The active principle can also be in the form of a complex with a cyclodextrin, for example $\alpha$-, $\beta$- or $\gamma$-cyclodextrin or 2-hydroxypropyl-$\beta$-cyclodextrin.

The active principle can also be formulated in the form of microcapsules or microspheres, optionally with one or more supports or additives.

Among the sustained-release forms which are useful in the case of chronic treatments, it is possible to use implants. These can be prepared in the form of an oily suspension or in the form of a suspension of microspheres in an isotonic medium.

In each dosage unit, the active principle of formula (I) is present in the amounts suited to the daily doses envisaged. In general, each dosage unit is appropriately adjusted according to the dosage and the type of administration envisaged, for example tablets, gel capsules and the like, sachets, ampules, syrups and the like, or drops, such that a dosage unit contains from 0.1 to 1000 mg of active principle, preferably from 0.5 to 250 mg, which needs to be administered 1 to 4 times a day.

Although these doses are examples of average situations, there may be special cases in which higher or lower doses are appropriate, and such doses also form part of the invention. According to the usual practice, the dosage which is appropriate to each patient is determined by the doctor according to the mode of administration, and the age, weight and response of the said patient.

According to another of its aspects, the present invention relates to the use of the compounds of formula (I), or of one of the pharmaceutically acceptable salts, solvates and/or hydrates thereof, for the preparation of medicinal products intended for treating any pathology in which substance P and the human $NK_1$ receptors are involved.

According to another of its aspects, the present invention relates to the use of the compounds of formula (I), or one of the pharmaceutically acceptable salts, solvates and/or hydrates thereof, for the preparation of medicinal products intended for treating pathologies of the respiratory, gastrointestinal, urinary, immune or cardiovascular system and of the central nervous system, as well as for pain, migraine, inflammations, nausea and vomiting, and skin diseases.

For example and in a non-limiting manner, the compounds of formula (I) are useful:

as analgesics, in particular in the treatment of traumatic pain such as post-operative pain; neuralgia of the brachial plexus; chronic pain such as arthritic pain caused by osteoarthritis, rheumatoid arthritis or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, neuropathies induced by a chemotherapy, AIDS-related neuropathies, occipital neuralgia, geniculate neuralgia or glossopharyngeal neuralgia; the illusory pain of amputees; various forms of headache such as chronic or acute migraine, temporomandibular pain, maxillary sinus pain, facial neuralgism or odontalgia; pain experienced by cancer sufferers; pain of visceral origin; gastrointestinal pain; pain caused by compression of a nerve, pain caused by intensive sporting activity; dysmenorrhoea; menstrual pain; pain caused by meningitis or arachnoiditis; musculoskeletal pain; pain in the lower back caused by a spinal stenosis, a prolapsed disc or sciatica; pain experienced by angina sufferers; pain caused by an ankylosing spondylitis; pain associated with gout; pain associated with burns, cicatrization or pruriginous dermatosis; thalamic pain;

as anti-inflammatory agents, in particular for treating inflammations in asthma, influenza, chronic bronchitis (in particular obstructive chronic bronchitis and COPD (chronic obstructive pulmonary disease)), coughing, allergies, bronchospasm and rheumatoid arthritis; inflammatory diseases of the gastrointestinal system, for example Crohn's disease, ulcerative colitis, pancreatitis, gastritis, intestinal inflammation, disorders caused by non-steroidal anti-inflammatory agents, inflammatory and secretory effects caused by bacterial infections, for example caused by Clostridium difficile; inflammatory skin diseases, for example herpes and eczema; inflammatory bladder diseases such as cystitis and urinary incontinence; ophthalmic inflammations such as conjunctivitis and vitreoretinopathy; dental inflammations such as gingivitis and periodontitis;

in the treatment of allergic diseases, in particular of the skin, such as urticaria, contact dermatitis, atopic dermatitis and respiratory diseases such as rhinitis;

in the treatment of diseases of the central nervous system, in particular psychoses such as schizophrenia, mania and dementia; cognitive disorders such as Alzheimer's disease, anxiety, AIDS-related dementia, diabetic neuropathies; depression; Parkinson's disease; drug dependency; substance abuse; consciousness disorders, sleeping disorders, disorders of the circadian rhythm, mood disorders and epilepsy; Down's syndrome; Huntington's chorea; stress-related somatic disorders; neurodegenerative diseases such as Pick's disease or Creutzfeldt-Jacob disease; disorders associated with panic, phobia or stress;

in the treatment of modifications of the permeability of the blood-brain barrier during inflammatory and autoimmune processes of the central nervous system, for example during AIDS-related infections;

as a muscle relaxant and antispasmodic agent;

in the treatment of acute or delayed and anticipated nausea and vomiting, for example nausea and vomiting induced by drugs such as the agents used in chemotherapy in the case of cancer; by radiation therapy during irradiation of the thorax or the abdomen in the treatment of cancer or carcinoidosis; by ingestion of poison; by toxins caused by metabolic or infectious disorders such as gastritis, or produced during a bacterial or viral gastrointestinal infection; during pregnancy; during vestibular disorders such as travel sickness, vertigo or Ménière's disease; in post-operative diseases; the nausea and vomiting induced by dialysis or by prostaglandins; by gastrointestinal obstructions; in reduced gastrointestinal motility; in visceral pain caused by myocardial infarction or peritonitis; in migraine; in altitude sickness; by ingestion of opiate analgesics such as morphine; in gastro-oesophageal reflux; in acidic indigestion or overconsumption of food or drink, in gastric acidity or acor, regurgitation, and heartburn, for example episodic or nocturnal heartburn or heartburn induced by a meal and dyspepsia;

in the treatment of diseases of the gastrointestinal system such as irritable bowel syndrome, gastric and duodenal ulcers, oesophageal ulcers, diarrhoea, hypersecretions, lymphomas, gastrites, gastro-oesophageal reflux, faecal incontinence, Hirschsprung's disease and food allergies;

in the treatment of skin diseases such as psoriasis, pruritus and burns, in particular sunburn;

in the treatment of diseases of the cardiovascular system such as hypertension, the vascular aspects of migraine, oedema, thrombosis, angina pectoris, vascular spasms, circulatory diseases caused by vasodilation, Raynaud's disease, fibrosis, collagen diseases and atherosclerosis;

in the treatment of small-cell lung cancer; cerebral tumours and adenocarcinomas of the urogenital sphere;

demyelination diseases such as multiple sclerosis or amyotrophic lateral sclerosis;

in the treatment of diseases of the immune system associated with suppression or stimulation of the functions of the immune cells, for example rheumatoid arthritis, psoriasis, Crohn's disease, diabetes, lupus and rejection reactions after transplantation;

in the treatment of miction disorders, in particular pollakiuria;

in the treatment of histiocytic reticulosis, for instance in lymphatic tissues;

as an anorexigenic agent;

in the treatment of emphysema; Reiter's disease; haemorrhoids;

in the treatment of ocular diseases such as glaucoma, ocular hypertension, myosis and excessive lachrymal secretion;

in the treatment or prevention of an epileptic fit, cranial trauma, spinal cord trauma, cerebral ischaemic lesions caused by vascular attack or occlusion;

in the treatment of disorders of heart rate and cardiac rhythm, in particular those occasioned by pain or stress;

in the treatment of sensitive skin and for preventing or combating irritation of the skin or mucous membranes, dandruff, erythema or pruritus;

in the treatment of neurological skin disorders such as lichens, prurigo, pruriginous toxidermia and severe pruritus of neurogenic origin;

in the treatment of ulcers and of all diseases caused by Helicobacter pylori or a urease-positive gram-negative bacterium;

in the treatment of diseases caused by angiogenesis or in which angiogenesis is a symptom;

in the treatment of ocular and/or palbebral algia and/or ocular or palbebral dysesthesia;

as an antiperspirant.

The present invention also includes a method for treating the said complaints at the doses indicated above.

The pharmaceutical compositions according to the present invention can also contain other active products that are useful for treating the diseases or disorders indicated above, for example bronchodilators, antitussive agents, antihistamines, anti-inflammatory agents, anti-emetic agents and chemotherapy agents.

The following abbreviations are used in the Preparations and in the Examples:

DMF: dimethylformamide
DMSO: dimethyl sulphoxide
DCM: dichloromethane
THF: tetrahydrofuran
ether: diethyl ether
hydrochloric ether: saturated solution of hydrochloric acid in diethyl ether
BOP: benzotriazol-1-yloxytris(dimethylamino) phosphonium hexafluorophosphate
m.p.: melting point
b.p.: boiling point
RT: room temperature
silica H: 60H silica gel sold by Merck (Darmstadt).

The proton nuclear magnetic resonance ($^1$H NMR) spectra are recorded at 200 MHz in DMSO-$d_6$, using the DMSO-$d_6$ peak as reference. The chemical shifts δ are indicated in parts per million (ppm). The signals observed are expressed as follows: s: singlet; bs: broad singlet; t: triplet; q: quartet; m: multiplet.

Preparation 1.1

3-(3,4-Dichlorophenyl)-3-(2-hydroxyethyl) piperidine, (−) isomer (II*): E = H; Ar = 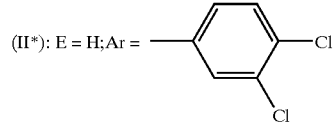

The preparation of this compound is described in patent application EP-A-0 591 040.

Preparation 1.2

3-(3,4-Dimethylphenyl)-3-[2-(2-tetrahydropyranyloxy)ethyl]piperidine (II): E = 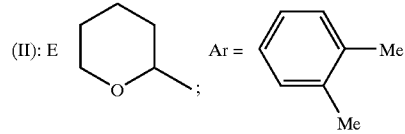

A) 2-(3,4-Dimethylphenyl)-4-(2-tetrahydropyranyloxy) butanenitrile 6.6 g of 60% sodium hydride in oil are added portionwise at RT to a solution of 20 g of 3,4-dimethylphenylacetonitrile in 100 ml of anhydrous THF, and the mixture is left stirring at RT for 2 hours. 29 g of 1-bromo-2-(2-tetrahydropyranyloxy)ethane are then added dropwise and the mixture is left stirring at RT for 2 days. The reaction mixture is poured onto ice and extracted with EtOAc, the organic phase is washed with water and with saturated NaCl solution and dried over $Na_2SO_4$, and the solvent is evaporated off under vacuum. The residue is chromatographed on silica gel, eluting with toluene and then with a gradient of a toluene/EtOAc mixture from (99/1; v/v) to (90/10; v/v). 17 g of the expected product are obtained.

B) Methyl 4-cyano-4-(3,4-dimethylphenyl)-6-(2-tetrahydropyranyloxy)hexanoate 0.3 ml of a 40% solution of benzyltrimethylammonium hydroxide (Triton®B) in MeOH is added to a mixture of 17 g of the compound obtained in the above step and 11 ml of methyl acrylate in 30 ml of dioxane, and the mixture is left stirring at RT for 48 hours. The reaction mixture is concentrated under vacuum, the residue is taken up in aqueous 0.5N HCl solution and extracted with ether, the organic phase is washed with aqueous 10% $Na_2CO_3$ solution and dried over $Na_2SO_4$, and the solvent is evaporated off under vacuum. 23 g of the expected product are obtained.

C) 5-(3,4-Dimethylphenyl)-5-[2-(2-tetrahydropyranyl-oxy)ethyl]-2-piperidone 40 ml of 20% aqueous ammonia solution are added to a solution of 23 g of the compound obtained in the above step in 250 ml of 95% EtOH, followed by addition of Raney® nickel. This mixture is then hydrogenated for 24 hours at 40°

C. and at a pressure of 16 bar. The catalyst is filtered off over Celite® and the filtrate is concentrated under vacuum. 22 g of the expected product are obtained.

D) 3-(3,4-Dimethylphenyl)-3-[2-(2-tetrahydropyranyloxy) ethyl]piperidine 22 g of the compound obtained in the above step are added to a suspension of 10 g of lithium aluminium hydride in 200 ml of THF, followed by refluxing for 2 hours. After cooling to RT, 10 ml of water and 80 ml of THF are added, followed by 10 ml of 4N NaOH and 30 ml of water. The mineral salts are filtered off over Celite® and the filtrate is concentrated under vacuum. 15 g of the expected product are obtained.

Preparation 2.1

3,5-Dichlorophenylacetic acid (III): $R_1$=Cl.

A) 3,5-Dichlorobenzyl chloride

A solution of 12.5 g of thionyl chloride in 20 ml of chloroform is added dropwise, at RT, to a solution of 14.5 g of 3,5-dichlorobenzyl alcohol in 150 ml of chloroform, followed by heating at 40–50° C. for 8 hours and stirring at RT overnight. The mixture is concentrated under vacuum to give 16 g of the expected product, which is used without further processing.

B) 3,5-Dichlorophenylacetonitrile

A solution of 6.5 g of potassium cyanide in 50 ml of water is added to a solution of 16 g of the compound obtained in the above step in 50 ml of EtOH, and the mixture is refluxed for 4 hours. The resulting mixture is concentrated under vacuum, the residue is taken up in water and extracted with ether, the organic phase is washed with water and dried over $Na_2SO_4$, and the solvent is evaporated off under vacuum. The residue is chromatographed on silica H, eluting with a heptane/toluene mixture (50/50; v/v) and then with toluene. 7 g of the expected product are obtained, which product is used without further processing.

C) 3,5-Dichlorophenylacetic acid

A solution of 8.4 g of KOH in 10 ml of water is added to a solution of 7 g of the compound obtained in the above step in 50 ml of EtOH, followed by refluxing for 5 hours. This mixture is concentrated under vacuum, the residue is taken up in water and the aqueous phase is washed with ether, acidified to pH=1 by addition of concentrated HCl and left stirring at RT overnight. The crystalline product formed is spin-dried, washed with water and dried under vacuum at 60° C. 7 g of the expected product are obtained; m.p.= 112–114.5° C.

Preparation 2.2

3,5-Diethylphenylacetic acid (III): $R_1$=Et.

A) 3,5-Diethylbromobenzene

A mixture of 20 g of 4-bromo-2,6-diethylaniline, 160 ml of acetic acid, 100 ml of concentrated HCl solution, 30 ml of water and 100 ml of EtOH is cooled to −5° C., a solution of 6.6 g of sodium nitrite in 25 ml of water is added dropwise and the mixture is left stirring at RT for 30 minutes. The reaction mixture is poured into 170 ml of 50% $H_3PO_2$ cooled to 0° C. and is left stirring for 2 hours at 0° C. and then for 48 hours at RT. The reaction mixture is extracted with ether, the organic phase is washed with water, with 1N NaOH solution, with water and dried over $Na_2SO_4$, and the solvent is evaporated off under vacuum. The residue is chromatographed on silica gel, eluting with cyclohexane. 18 g of the expected product are obtained.

B) 3,5-Diethylbenzonitrile

A mixture of 24.7 g of the compound obtained in the above step and 12 g of cuprous cyanide in 70 ml of DMF is refluxed for 15 hours. After cooling to RT, the reaction mixture is poured into 50 ml of water and left stirring at RT until a gum forms. The mixture is cooled on an ice bath, 150 ml of ethylenediamine are added and this mixture is left stirring at RT for 2 hours. The mixture is extracted with EtOAc, the organic phase is washed with water and dried over $Na_2SO_4$ and the solvent is evaporated off under vacuum. The residue is chromatographed on silica gel, eluting with a cyclohexane/EtOAc mixture (95/5; v/v). 12 g of the expected product are obtained.

C) 3,5-Diethylbenzoic acid

A solution of 22 g of KOH in 15 ml of water is added to a solution of 12 g of the compound obtained in the above step in 60 ml of EtOH, followed by refluxing for 24 hours. The reaction mixture is concentrated under vacuum, the residue is extracted with water, the aqueous phase is washed with ether and acidified to pH=2 by addition of concentrated HCl, and the precipitate formed is spin-dried, washed with water and dried under vacuum. 13 g of the expected product are obtained.

D) Methyl 3,5-diethylbenzoate

A mixture of 13 g of the compound obtained in the above step in 90 ml of MeOH and 10 drops of $H_2SO_4$ is refluxed for 48 hours. The reaction mixture is concentrated under vacuum, the residue is taken up in water, neutralized by addition of 10% $NaHCO_3$ solution and extracted with ether, the organic phase is washed with 10% $NaHCO_3$ solution, with water and dried over $Na_2SO_4$, and the solvent is evaporated off under vacuum. 12 g of the expected product are obtained.

E) 3,5-Diethylbenzyl alcohol

A suspension of 2.5 g of lithium aluminium hydride in 50 ml of THF is cooled to 0° C., a solution of 12 g of the compound obtained in the above step in 50 ml of THF is added dropwise and the mixture is left stirring for 30 minutes. The reaction mixture is hydrolysed by addition of 2.5 ml of water, 2.5 ml of 4N NaOH and 7.5 ml of water. The mineral salts are filtered off and the filtrate is concentrated under vacuum. 10.9 g of the expected product are obtained, which product is used without further processing.

F) 3,5-Diethylbenzyl methanesulphonate

A solution of 8.4 g of methanesulphonyl chloride in 50 ml of DCM is added dropwise at RT to a solution of 10.9 g of the compound obtained in the above step and 7.4 g of triethylamine in 100 ml of DCM, and the mixture is left stirring for 30 minutes. The reaction mixture is concentrated under vacuum, the residue is taken up in water and extracted with ether, the organic phase is washed with water and dried over $Na_2SO_4$, and the solvent is evaporated off under vacuum. 16 g of the expected product are obtained, which product is used without further processing.

G) 3,5-Diethylphenylacetonitrile

A solution of 5.15 g of potassium cyanide in 20 ml of water is added to a solution of 16 g of the compound obtained in the above step in 100 ml of DMF and the mixture is heated at 80° C. for 1 hour. The reaction mixture is concentrated under vacuum, the residue is taken up in water and extracted with ether, the organic phase is washed with water and dried over $Na_2SO_4$, and the solvent is evaporated off under vacuum. The residue is chromatographed on silica H gel, eluting with DCM. 3 g of the expected product are obtained.

H) 3,5-Diethylphenylacetic acid

A solution of 7.8 g of KOH in 10 ml of water is added to a solution of 3 g of the compound obtained in the above step in 50 ml of EtOH, followed by refluxing for 5 hours. This mixture is concentrated under vacuum, the residue is taken up in water and the aqueous phase is washed with ether, acidified to pH=1 by addition of concentrated HCl and left stirring at RT overnight. The crystalline product formed is spin-dried, washed with water and dried under vacuum. 2.5 g of the expected product are obtained.

$^1$H NMR: δ (ppm): 1.1:t:6H; 2.4:q:4H; 3.4:s:2H; 6.8:m:3H; 12.2:bs:1H.

Preparation 3.1

2-(4-Piperidyl)isobutyramide hydrochloride (VII), HCl:

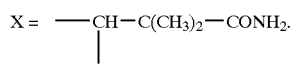

A) 2-Methyl-2-(4-pyridyl)propionitrile

A mixture of 3 g of 4-pyridylacetonitrile hydrochloride in 50 ml of DMF is cooled to 0° C., 2.6 g of 60% sodium hydride in oil are added portionwise and the mixture is left stirring at RT for 2 hours. The reaction mixture is cooled on an ice bath, 6 g of methyl iodide are added dropwise and the mixture is left stirring at RT overnight. The reaction mixture is poured onto a water/ice mixture and extracted with ether, the organic phase is washed with saturated NaCl solution, dried over MgSO$_4$ and filtered, and the solvent is evaporated off under vacuum. The residue is chromatographed on silica H gel, eluting with DCM and then with a DCM/MeOH mixture (98/2; v/v). 2.39 g of the expected product are obtained in the form an oil which crystallizes.

B) 2-(4-Pyridyl)isobutyramide hydrochloride

A mixture of 2.39 g of the compound obtained in the above step and 10 ml of concentrated H$_2$SO$_4$ solution is heated at 100° C. for 15 minutes. The reaction mixture is cooled to RT, 50 g of ice are added, this mixture is basified to pH=14 by addition of concentrated NaOH solution, the mineral salts are filtered off, the filtrate is extracted with EtOAc and then with DCM, the combined organic phases are dried over MgSO$_4$ and filtered, and the solvents are evaporated off under vacuum (m.p.=134° C., base). The product obtained is dissolved in acetone and acidified to pH=1 by addition of hydrochloric ether, and the precipitate formed is spin-dried. 2.9 g of the expected product are obtained.

C) 2-(4-Piperidyl)isobutyramide hydrochloride

A mixture of 2.9 g of the compound obtained in the above step, 1 g of PtO$_2$ and 50 ml of MeOH is hydrogenated for 3 days at 60° C. under a pressure of 60 bar. The catalyst is filtered off over Celite® and washed with MeOH, and the filtrate is concentrated under vacuum. The residue is taken up in acetonitrile and the precipitate formed is spin-dried and washed with acetonitrile and then with ether. 2.5 g of the expected product are obtained; m.p.>260° C.

Preparation 3.2

2-(1-Piperazinyl)isobutyramide dihydrochloride (VII), 2HCl:

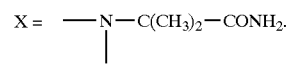

A) 2-(4-Benzyl-1-piperazinyl)-2-methylpropionitrile 4.5 ml of acetone, 20 g of dry MgSO$_4$, 10 g of N,N-dimethylacetamide, 10 g of 1-benzylpiperazine and 9.5 ml of 2-hydroxyisobutyronitrile are mixed together and heated at 45° C. for 48 hours with vigorous stirring. The reaction mixture is poured onto ice and left stirring for 30 minutes. The mixture is extracted with ether, the organic phase is washed several times with water and dried over Na$_2$SO$_4$, and the solvent is evaporated off under vacuum. 13 g of the expected product are obtained.

B) 2-(4-Benzyl-1-piperazinyl)isobutyramide dihydrochloride

A mixture of 13 g of the compound obtained in the above step and 130 ml of 90% H$_2$SO$_4$ solution are heated rapidly at 110° C. for 30 minutes. After cooling to RT, the reaction mixture is poured onto ice and basified to pH=10 by addition of concentrated NH$_4$OH solution, and the crystalline product formed is spin-dried. The product is dissolved in DCM, the organic phase is dried over MgSO$_4$ and the solvent is evaporated off under vacuum. The product is taken up in hydrochloric ether and the precipitate formed is spin-dried. 9.5 g of the expected product are obtained.

C) 2-(1-Piperazinyl)isobutyramide dihydrochloride

A mixture of 1.3 g of the compound obtained in the above step and 0.18 g of 10% palladium-on-charcoal in 30 ml of 95% EtOH is hydrogenated overnight at RT and at atmospheric pressure. The catalyst is filtered off over Celite® and the filtrate is concentrated under vacuum. 0.6 g of the expected product is obtained.

Preparation 3.3

1-(1-Piperazinyl)cyclohexanecarboxamide dihydrochloride

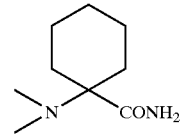

(VII), 2HCl: X=

A) 1-(4-Benzyl-1-piperazinyl)cyclohexanecarbonitrile 5.7 g of cyclohexanone, 20 g of dry MgSO$_4$, 10 g of N,N-dimethylacetamide, 10 g of 1-benzylpiperazine and 9.5 ml of 2-hydroxyisobutyronitrile are mixed together and heated at 45° C. for 48 hours with vigorous stirring. The reaction mixture is poured onto ice and left stirring for 30 minutes. The mixture is extracted with ether, the organic phase is washed several times with water and dried over Na$_2$SO$_4$, and the solvent is evaporated off under vacuum. 15 g of the expected product are obtained.

B) 1-(4-Benzyl-1-piperazinyl)cyclohexanecarboxamide dihydrochloride

This compound is obtained according to the procedure described in step B of Preparation 3.2, starting with 15 g of the compound obtained in the above step and 50 ml of 90% H$_2$SO$_4$ solution. 5.5 g of the expected product are obtained.

C) 1-(1-Piperazinyl)cyclohexanecarboxamide dihydrochloride

This compound is obtained according to the procedure described in step C of Preparation 3.2, starting with 2.3 g of the compound obtained in the above step and 0.3 g of 10% palladium-on-charcoal in 30 ml of 95% EtOH. 1.6 g of the expected product are obtained.

Preparation 3.4

N,N-Dimethyl-2-(1-piperazinyl)isobutyramide diformate (VII), 2HCO$_2$H:

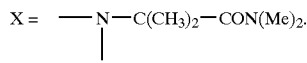

A) N,N-Dimethyl-2-(4-benzyl-1-piperazinyl)isobutyramide 1.44 g of 60% sodium hydride in oil are added portionwise to a mixture of 2.6 g of the compound obtained in step B of Preparation 3.2 (free base) in 50 ml of anhydrous THF. 1.3 ml of methyl iodide are then added dropwise and this mixture is left stirring at RT for 4 hours. The reaction mixture is poured into water and extracted with ether, the organic phase is dried over MgSO$_4$ and the solvents are evaporated off under vacuum. 1.8 g of the expected product are obtained.

B) N,N-Dimethyl-2-(1-piperazinyl)isobutyramide diformate 2 g of ammonium formate and 0.5 g of 5% palladium-on-charcoal are added to a solution of 1.8 g of the compound obtained in the above step in 30 ml of MeOH, and the mixture is left stirring at RT for 4 hours. The catalyst is filtered off over Celite® and the filtrate is concentrated under vacuum. The residue is taken up in EtOAc and the precipitate formed is spin-dried, washed with EtOAc and dried. 1.2 g of the expected product are obtained.

Preparation 3.5

1-(4-Piperidyl)cyclohexanecarboxamide hydrochloride (VII), HCl: X=

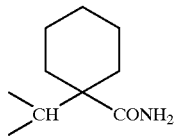

A) 1-(4-Pyridyl)cyclohexanecarbonitrile

A mixture of 3 g of 4-pyridylacetonitrile hydrochloride in 50 ml of DMF is cooled to 0° C., 2.6 g of 60% sodium hydride in oil are added portionwise and the mixture is left stirring at RT for 1 hour 30 minutes. The reaction mixture is cooled on an ice bath, 2.7 ml of 1,5-dibromopentane are added dropwise and this mixture is left stirring at RT for 48 hours. The reaction mixture is poured into saturated NH$_4$Cl solution and extracted with ether, the organic phase is washed three times with water and dried over MgSO$_4$, and the solvent is evaporated off under vacuum. The residue is chromatographed on silica H gel, eluting with DCM and then with a DCM/MeOH mixture (98/2; v/v). 2.5 g of the expected product are obtained; m.p.=79° C.

B) 1-(4-Pyridyl)cyclohexanecarboxamide hydrochloride

A mixture of 2.5 g of the compound obtained in the above step and 15 ml of concentrated H$_2$SO$_4$ solution is heated at 100° C. for 15 minutes. The reaction mixture is cooled to RT, poured onto ice and basified to pH=14 by addition of concentrated NaOH solution, and the precipitate formed is spin-dried, washed with water and dried. The product obtained is dissolved in acetone, acidified to pH=1 by addition of hydrochloric ether and left stirring at RT for 30 minutes, and the precipitate formed is spin-dried. 3 g of the expected product are obtained; m.p.=224° C. (dec.).

C) 1-(4-Piperidyl)cyclohexanecarboxamide hydrochloride

A mixture of 2.9 g of the compound obtained in the above step, 0.5 g of PtO$_2$ and 50 ml of MeOH is hydrogenated for 3 days at 60° C., at a pressure of 80 bar. The catalyst is filtered off over Celite® and the filtrate is concentrated under vacuum. The residue is taken up in acetonitrile and left stirring at RT for 1 hour, and the precipitate formed is spin-dried. 2.7 g of the expected product are obtained; m.p.=235° C.

Preparation 3.6

N,N-Dimethyl-2-(4-piperidyl)isobutyramide hydrochloride (VII), HCl:

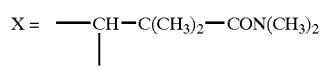

A) Ethyl 1-benzyl-4-piperidinecarboxylate 30 g of benzyl bromide are added dropwise to a mixture of 25 g of ethyl isonipecotate and 25 g of K$_2$CO$_3$ in 125 ml of DMF, while maintaining the temperature of the reaction mixture between 25 and 30° C., and the resulting mixture is then stirred at RT for 1 hour. The reaction mixture is poured onto 1 litre of ice-cold water and extracted twice with ether, the organic phase is washed with water and dried over MgSO$_4$, and the solvent is evaporated off under vacuum. The resulting oil obtained is distilled off under reduced pressure. 29.2 g of the expected product are obtained; b.p.=120–122° C. at 2.7 Pa.

B) 2-(1-Benzyl-4-piperidyl)-2-propanol

A solution of 24.73 g of the compound obtained in the above step in 100 ml of benzene is added dropwise, while maintaining the temperature of the medium between 25 and 30° C., to 200 ml of a 1.5M solution of methyllithium, as a complex with lithium bromide, in ether, under an argon atmosphere, followed by refluxing for 48 hours. The reaction mixture is cooled to RT and then poured into 400 ml of saturated NH$_4$Cl solution in water, which has been cooled beforehand on an ice bath. The mixture is extracted three times with ether, the combined organic phases are dried over MgSO$_4$ and the solvent is evaporated off under vacuum. The residue is dissolved in 100 ml of acetone, cooled to 10° C. and acidified to pH=1 by addition of hydrochloric ether, and the precipitate formed is spin-dried and washed with an acetone/ether mixture (50/50; v/v). 24.5 g of the expected product are obtained in the form of the hydrochloride; m.p.=204° C. To free the base, the hydrochloride is taken up in concentrated NaOH solution, extracted with ether and dried over MgSO$_4$, and the solvent is evaporated off under vacuum. 21 g of the expected product are obtained; m.p.=66° C.

C) 2-(1-Benzyl-4-piperidyl)-2-methylpropionic acid

A mixture of 5.98 g of 95% sulphuric acid and 4.42 g of fuming sulphuric acid containing 30% SO$_3$ is cooled to 3° C., and a solution of 2 g of the compound obtained in the above step in 1.55 g of 100% formic acid is added dropwise while maintaining the temperature below 10° C. The mixture is left stirring for 2 hours at 3–5° C. and is then allowed to return to RT and is left overnight at RT. The reaction mixture is poured onto ice, the pH is brought to 6.5 by addition of concentrated NaOH solution and by addition of concentrated NH$_4$OH solution and extracted three times with DCM, the combined organic phases are dried over MgSO$_4$ and the solvent is evaporated off under vacuum. The residue is taken up in acetone and the precipitate is spin-dried and dried. 1.22 g of the expected product are obtained; m.p.=195° C.

D) N,N-Dimethyl-2-(1-benzyl-4-piperidyl)isobutyramide hydrochloride

A mixture of 1.2 g of the compound obtained in the above step, 0.8 ml of triethylamine, 2.8 ml of a 2M solution of dimethylamine in THF and 2.5 g of BOP in 20 ml of DCM is stirred for 1 hour at RT. The reaction mixture is concentrated under vacuum, the residue is taken up in ether, the organic phase is washed with water, with 1N NaOH solution, with saturated NaCl solution and dried over MgSO$_4$, and the solvent is evaporated off under vacuum. The residue is chromatographed on silica H gel, eluting with DCM and then with a gradient of a DCM/MeOH mixture from (99/1; v/v) to (95/5; v/v). The product obtained is dissolved in acetone and acidified to pH=1 by addition of hydrochloric ether, and the precipitate formed is spin-dried and dried. 0.8 g of the expected product is obtained; m.p.=229° C.

E) N,N-Dimethyl-2-(4-piperidyl)isobutyramide hydrochloride

A mixture of 0.8 g of the compound obtained in the above step and 0.2 g of 10% palladium-on-charcoal in 20 ml of MeOH is hydrogenated overnight at atmospheric pressure and at RT. The catalyst is filtered off over Celite® and the filtrate is concentrated under vacuum. The residue is dissolved in acetonitrile, ether is added and the precipitate formed is spin-dried and dried. 0.51 g of the expected product is obtained; m.p.=258° C.

Preparation 3.7

1-(4-Piperidyl)cyclopropanecarboxamide hydrochloride

(VII), HCl: X=

A) 1-(4-Pyridyl)cyclopropanecarbonitrile 3.5 g of 4-pyridylacetonitrile are added to a mixture of 2.5 g of sodium amide in 80 ml of DCM, followed by 2.6 ml of 1,2-dibromoethane, and the mixture is stirred overnight at RT. The reaction mixture is poured into water and extracted with EtOAc, the organic phase is washed with water and dried over Na$_2$SO$_4$, and the solvents are evaporated off under vacuum. The residue is chromatographed on silica gel, eluting with DCM and then with a DCM/MeOH mixture from (99/1; v/v) to (95/5; v/v). 2.5 g of the expected product are obtained.

B) 1-(4-Pyridyl)cyclopropanecarboxamide hydrochloride

A mixture of 2.5 g of the compound obtained in the above step and 20 ml of 96% H$_2$SO$_4$ solution is heated rapidly to 100° C. and left stirring for 1 hour at 100° C. After cooling to RT, the reaction mixture is poured onto ice and neutralized to pH=7 by addition of 20% NH$_4$OH solution, and the precipitate formed is spin-dried, washed with water and dried. The precipitate is dissolved in DCM, acidified to pH=1 by addition of hydrochloric ether and the precipitate formed is spin-dried. 1.8 g of the expected product are obtained.

C) 1-(4-Piperidyl)cyclopropanecarboxamide hydrochloride

A mixture of 1.8 g of the compound obtained in the above step and 0.6 g of PtO$_2$ in 50 ml of MeOH is hydrogenated for 15 hours at 80° C. and at a pressure of 100 bar. The catalyst is filtered off over Celite®, the filtrate is concentrated under vacuum to a volume of 5 ml and acetonitrile is added until crystallization occurs. 1.7 g of the expected product are obtained after spin-drying and then drying.

Preparation 3.8

2-Methyl-1-(4-morpholinyl)-2-(4-piperidyl)-1-propanone hydrochloride

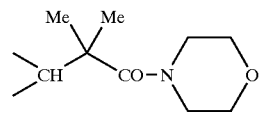

(VII), HCl: X=

A) 2-(1-Benzyl-4-piperidyl)-2-methyl-1-(4-morpholinyl)-1-propanone hydrochloride A mixture of 1 g of the compound obtained in step C of Preparation 3.6 and 1.2 ml of thionyl chloride in 20 ml of 1,2-dichloroethane is heated at 80° C. for 3 hours. The reaction mixture is concentrated under vacuum, the acid chloride thus obtained is dissolved in 20 ml of DCM, this solution is added to a mixture of 0.7 g of morpholine and 1.6 ml of triethylamine in 20 ml of DCM cooled beforehand to 0° C., and the resulting mixture is stirred at RT for 24 hours. The reaction mixture is concentrated under vacuum, the residue is extracted with ether, the organic phase is washed with 1N NaOH solution, with water and dried over MgSO$_4$, and the solvent is evaporated off under vacuum. The product obtained is dissolved in acetone and acidified to pH=1 by addition of hydrochloric ether, and the precipitate formed is spin-dried and dried. 0.7 g of the expected product is obtained.

B) 2-Methyl-1-(4-morpholinyl)-2-(4-piperidyl)-1-propanone hydrochloride

A mixture of 0.7 g of the compound obtained in the above step, 0.7 g of ammonium formate and 0.2 g of 10% palladium-on-charcoal in 10 ml of MeOH is stirred at RT for 4 hours. The catalyst is filtered off over Celite® and the filtrate is concentrated under vacuum. The residue is dissolved in acetonitrile, ether is added and the precipitate formed is spin-dried and dried. 0.46 g of the expected product is obtained; m.p.=225° C.

EXAMPLE 1

3-[2-[4-(1-Carbamoyl-1-methylethyl)-1-piperidyl]ethyl]-3-(3,4-dichlorophenyl)-1-[2-(3,5-dimethylphenyl)-acetyl]piperidine hydrochloride monohydrate, (−) isomer

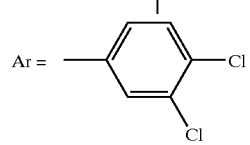

(I), HCl:

A) 3-(3,4-Dichlorophenyl)-3-(2-hydroxyethyl)-1-[2-(3,5-dimethylphenyl)acetyl]piperidine, single isomer 2.3 ml of triethylamine are added to a mixture of 2.0 g of 3,5-dimethylphenylacetic acid in 100 ml of DCM at RT, followed by 3 g of the compound obtained in Preparation 1 and 5.3 g of BOP, and this mixture is stirred for 1 hour at RT. The reaction mixture is concentrated under vacuum, the residue is extracted with ether, the organic phase is washed with water, with 2N HCl solution, with water, with aqueous 10% NaOH solution, dried over $Na_2SO_4$ and filtered, and the filtrate is concentrated under vacuum. The residue is chromatographed on silica H gel, eluting with DCM and then with a DCM/MeOH mixture (98/2; v/v). 3.9 g of the expected product are obtained, which product is used in the following step without further processing.

B) 3-(3,4-Dichlorophenyl)-3-(formylmethyl)-1-[2-(3,5-dimethylphenyl)acetyl]piperidine, single isomer A solution of 0.25 ml of oxalyl chloride in 3 ml of DCM is cooled to –70° C., under a nitrogen atmosphere, a solution of 0.35 ml of DMSO in 3 ml of DCM is added dropwise, followed by a solution of 0.5 g of the compound obtained in the above step in 5 ml of DCM, and the mixture is stirred for 15 minutes at –50° C. 0.9 ml of triethylamine is then added and the mixture is left stirring while allowing it to return to RT. The reaction mixture is washed with water, with 1N HCl solution and with 10% $NaHCO_3$ solution, the organic phase is dried over $Na_2SO_4$ and filtered, and the filtrate is concentrated under vacuum. 0.5 g of the expected product is obtained, which product is used in the following step without further processing.

C) 3-[2-[4-(1-Carbamoyl-1-methylethyl)-1-piperidyl]ethyl-3-(3,4-dichlorophenyl)-1-[2-(3,5-dimethylphenyl)-acetyl]piperidine hydrochloride monohydrate, (–) isomer 0.08 ml of acetic acid is added at RT and under a nitrogen atmosphere to a solution of 0.24 g of the compound obtained in Preparation 3.1 (free base) in 3 ml of MeOH, followed by a solution of 0.5 g of the compound obtained in the above step in 5 ml of MeOH. After 5 minutes, 0.08 g of sodium cyanoborohydride is added and the mixture is left stirring at RT overnight. The reaction mixture is poured into aqueous 10% $NaHCO_3$ solution and extracted with ether, the organic phase is washed with water, dried over $N_2SO_4$ and filtered, and the filtrate is concentrated under vacuum. The residue is chromatographed on silica H gel, eluting with DCM and then with a gradient of a DCM/MeOH mixture from (99/1; v/v) to (90/10; v/v). The product obtained is dissolved in DCM, acidified to pH=1 by addition of hydrochloric ether and concentrated under vacuum. 0.5 g of the expected product is obtained after trituration from ether, spin-drying and drying under vacuum.

$\alpha_D^{20}$=–27.7° (c=1; MeOH)

$^1$H NMR: δ (ppm): 0.7 to 1.2; bs:6H; 1.2 to 2.4; m:16H; 2.5 to 4.8:m:12H; 6.5 to 8.0:m:8H; 10.2:bs:1H.

EXAMPLE 2

3-[2-[4-(1-Carbamoyl-1-methylethyl)-1-piperazinyl]ethyl-3-(3,4-dichlorophenyl)-1-[2-(3,5-dimethylphenyl)acetyl]piperidine dihydrochloride.2.7 $H_2O$, (–) isomer (I), 2HCl:

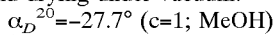

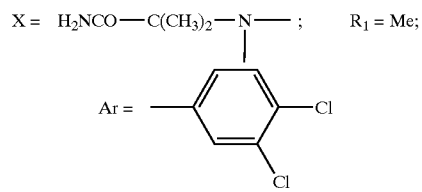

0.23 g of the compound obtained in Preparation 3.2 (free base) is added, at RT and under a nitrogen atmosphere, to a solution of 0.5 g of the compound obtained in step B of Example 1 in 20 ml of DCM, followed by 0.1 ml of acetic acid, and the mixture is stirred at RT for 30 minutes. 0.55 g of sodium triacetoxyborohydride is then added and the mixture is left stirring at RT overnight. Aqueous 10% $Na_2CO_3$ solution is added and the reaction mixture is stirred for 15 minutes at RT. The reaction mixture is extracted with DCM, the organic phase is washed with aqueous 10% $Na_2CO_3$ solution, dried over $Na_2SO_4$ and filtered, and the filtrate is concentrated under vacuum. The residue is chromatographed on silica gel, eluting with DCM and then with a gradient of a DCM/MeOH mixture from (99/1; v/v) to (95/5; v/v). The product obtained is dissolved in DCM and acidified to pH=1 by addition of hydrochloric ether, and the precipitate formed is spin-dried, washed with ether and dried under vacuum. 0.4 g of the expected product is obtained.

$\alpha_d^{20}$=–37° (c=1; MeOH)

$^1$H NMR: δ (ppm): 0.6 to 2.3:m:18H; 2.3 to 4.7:m:16H; 6.4 to 8.0:m:8H.

EXAMPLE 3

3-[2-[4-(1-N,N-Dimethylcarbamoyl-1-methylethyl)-1-piperazinyl]ethyl]-3-(3,4-dichlorophenyl)-1-[2-(3,5-dimethylphenyl)acetyl]piperidine dihydrochloride 1.25 $H_2O$, (–) isomer

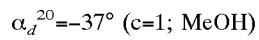

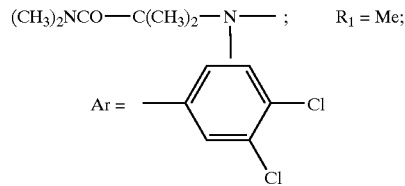

(I), 2HCl: X=

0.6 g of the compound obtained in step B of Example 1, 0.3 g of the compound obtained in Preparation 3.4, 0.1 ml of acetic acid and then 0.12 g of sodium cyanoborohydride are added, at RT, to 20 ml of MeOH and the mixture is stirred overnight at RT. Aqueous 10% $Na_2CO_3$ solution is added to the reaction mixture and the mixture is left stirring for 15 minutes. The mixture is extracted with EtOAc, the organic phase is washed with aqueous 10% $Na_2CO_3$ solution, with water, with saturated NaCl solution and dried over $Na_2SO_4$, and the solvent is evaporated off under vacuum. The residue is chromatographed on silica gel, eluting with DCM and then with a gradient of a DCM/MeOH mixture from (99/1; v/v) to (95/5; v/v). The product obtained is dissolved in DCM and acidified to pH=1 by addition of hydrochloric ether, and the precipitate formed is spin-dried, washed with ether and dried under vacuum. 0.4 g of the expected product is obtained.

$\alpha_d^{20}$=–28.4° (c=1; MeOH).

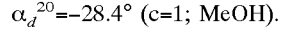

$^1$H NMR: δ (ppm): 0.7 to 2.3; m:18H; 2.35 to 4.7; m:22H; 6.5 to 7.8:m:6H; 10.3:s:1H.

EXAMPLE 4

3-[2-[4-(1-Carbamoyl-1-methylethyl)-1-piperidyl]ethyl]-3-(3,4-dichlorophenyl)-1-[2-(3,5-dichlorophenyl)acetyl]piperidine hydrochloride sesquihydrate, (−) isomer

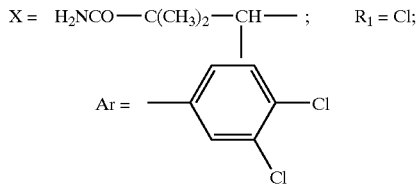

(I), HCl:

A) 3-(3,4-Dichlorophenyl)-3-(2-hydroxyethyl)-1-[2-(3,5-dichlorophenyl)acetyl]piperidine, single isomer 4.75 g of the compound obtained in Preparation 1, 3.55 g of the compound obtained in Preparation 2.1, 3.6 ml of triethylamine and then 8.4 g of BOP are added, at RT, to 150 ml of DCM and the mixture is left stirring at RT for 2 hours. The reaction mixture is concentrated under vacuum, the residue is extracted with EtOAc, the organic phase is washed with 1N HCl solution, with water, with 1N NaOH solution, with water, with saturated NaCl solution and dried over $Na_2SO_4$, and the solvent is evaporated off under vacuum. 8 g of the expected product are obtained, which product is used without further processing.

B) 3-(3,4-Dichlorophenyl)-3-(formylmethyl)-1-[2-(3,5-dichlorophenyl)acetyl]piperidine, single isomer This compound is prepared according to the procedure described in step B of Example 1, starting with 0.25 ml of oxalyl chloride in 6 ml of DCM, 0.38 ml of DMSO in 3 ml of DCM, 1 g of the compound obtained in the above step in 6 ml of DCM and then 1.5 ml of triethylamine. 1.0 g of the expected product is obtained, which product is used without further processing.

C) 3-[2-[4-(1-Carbamoyl-1-methylethyl)-1-piperidyl]ethyl]-3-(3,4-dichlorophenyl)-1-[2-(3,5-dichlorophenyl)acetyl]piperidine hydrochloride sesquihydrate, (−) isomer This compound is prepared according to the procedure described in step C of Example 1, starting with 0.25 g of the compound obtained in Preparation 3.1 (free base) in 3 ml of MeOH, 0.08 ml of acetic acid, 0.5 g of the compound obtained in the above step in 5 ml of MeOH and then 0.08 g of sodium cyanoborohydride. 0.52 g of the expected product is obtained.

$\alpha_D^{20} = -0.60$ (c 1; MeOH).

EXAMPLE 5

3-[2-[4-(1-Carbamoyl-1-methylethyl)-1-piperidyl]ethyl]-3-(3,4-dichlorophenyl)-1-[2-[3,5-bis(trifluoromethyl)phenyl]acetyl]piperidine hydrochloride monohydrate, (+) isomer (I), HCl:

X = H₂NCO—C(CH₃)₂—CH— ;   R₁ = CF₃;

-continued

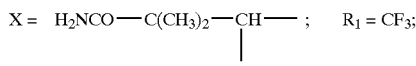

A) 3-(3,4-Dichlorophenyl)-3-(2-hydroxyethyl)-1-[2-[3,5-bis(trifluoromethyl)phenyl]acetyl]piperidine, single isomer 1.2 g of the compound obtained in Preparation 1, 1.2 g of 3,5-bis(trifluoromethyl)phenylacetic acid, 1.7 ml of triethylamine and then 2.16 g of BOP are added, at RT, to 50 ml of DCM and the mixture is stirred for 15 minutes. The reaction mixture is concentrated under vacuum, the residue is taken up in 1N HCl solution and extracted with ether, the organic phase is washed with 1N HCl solution, with water, with 1N NaOH solution, with water and dried over $Na_2SO_4$, and the solvent is evaporated off under vacuum. 2.1 g of the expected product are obtained, which product is used without further processing.

B) 3-(3,4-Dichlorophenyl)-3-(formylmethyl)-1-[2-[3,5-bis(trifluoromethyl)phenyl]acetyl]piperidine, single isomer 20 ml of DCM are cooled to −78° C., 1.5 g of the compound obtained in the above step, 0.45 ml of DMSO and then 0.3 ml of oxalyl chloride are added, under a nitrogen atmosphere, and the mixture is then left stirring at −78° C. for 30 minutes. 2 ml of triethylamine are then added and the mixture is stirred while allowing it to return to RT. 1N HCl solution is added to the reaction mixture, the resulting mixture is extracted with DCM, the organic phase is washed with 1N HCl solution, with water, with aqueous 10% $Na_2CO_3$ solution and dried over $Na_2SO_4$, and the solvent is evaporated off under vacuum. 1.5 g of the expected product are obtained, which product is used without further processing.

C) 3-[2-[4-(1-Carbamoyl-1-methylethyl)-1-piperidyl]ethyl]-3-(3,4-dichlorophenyl)-1-[2-[3,5-bis(trifluoromethyl)phenyl]acetyl]piperidine, hydrochloride monohydrate, (+) isomer A mixture of 0.35 g of the compound obtained in Preparation 3.1 and 0.4 g of $K_2CO_3$ in 10 ml of acetonitrile is refluxed for 3 hours. An insoluble material is filtered off and the filtrate is concentrated under vacuum. The product of Preparation 3.1 in the form of the free base thus obtained is dissolved in 3 ml of MeOH, 0.08 ml of acetic acid is added, followed by a solution of 0.5 g of the compound obtained in the above step in 5 ml of MeOH, and the mixture is left stirring at RT for 5 minutes. 0.08 g of sodium cyanoborohydride is then added and the mixture is left stirring overnight at RT. The reaction mixture is poured onto aqueous 10% $NaHCO_3$ solution and extracted with ether, the organic phase is washed with water and dried over $Na_2SO_4$, and the solvent is evaporated off under vacuum. The residue is chromatographed on silica H gel, eluting with DCM and then with a gradient of a DCM/MeOH mixture from (99/1; v/v) to (90/10; v/v). The product obtained is dissolved in DCM and acidified to pH=1 by addition of hydrochloric ether, and the precipitate formed is spin-dried. This gives 0.54 g of the product obtained after drying under vacuum.

$\alpha_D^{20} = +28.2°$ (c=1; MeOH).

¹H NMR: δ (ppm): 0.6 to 2.2:m:16H; 2.3 to 4.2:m:12H; 6.6 to 8.0:m:8H; 10.3:s:1H.

EXAMPLE 6

3-[2-[4-(1-N,N-Dimethylcarbamoyl-1-methylethyl)-1-piperidyl]ethyl]-3-(3,4-dichlorophenyl)-1-[2-(3,5-dimethylphenyl)acetyl]piperidine hydrochloride hemihydrate, (−) isomer (I), HCl:

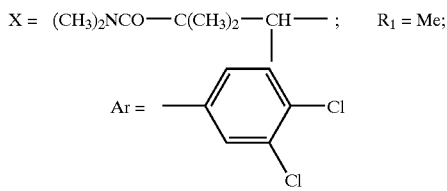

X = (CH$_3$)$_2$NCO—C(CH$_3$)$_2$—CH—; R$_1$ = Me;

Ar = (3,4-dichlorophenyl)

A mixture of 0.35 g of the compound obtained in Preparation 3.6 and 0.4 g of K$_2$CO$_3$ in 10 ml of acetonitrile is refluxed for 3 hours. An insoluble material is filtered off and the filtrate is concentrated under vacuum. The product of Preparation 3.6 in the form of the free base thus obtained is dissolved in 3 ml of MeOH, 0.1 ml of acetic acid is added, followed by a solution of 0.6 g of the compound obtained in step B of Example 1 in 5 ml of MeOH, and the mixture is left stirring at RT for 5 minutes. 0.1 g of sodium cyanoborohydride is then added and the mixture is left stirring at RT overnight. The reaction mixture is poured into aqueous 10% NaHCO$_3$ solution and extracted with ether, the organic phase is washed with water and dried over MgSO$_4$, and the solvent is evaporated off under vacuum. The residue is chromatographed on silica H gel, eluting with DCM and then with a gradient of a DCM/MeOH mixture from (99/1; v/v) to (90/10; v/v). The product obtained is dissolved in DCM and acidified to pH=1 by addition of hydrochloric ether, and the solvents are evaporated off under vacuum. 0.68 g of the expected product is obtained after trituration from ether, spin-drying and drying; m.p.=202° C.

$\alpha_D^{20}$=−27.1° (c=1; MeOH)

$^1$H NMR: δ (ppm): 0.6 to 2.5:m:23H; 2.5 to 4.6:m:18H; 6.4 to 7.8:m:6H; 10.1:s:1H.

EXAMPLE 7

3-[2-[4-(1-Carbamoyl-1-methylethyl)-1-piperidyl]ethyl]-3-(3,4-dichlorophenyl)-1-[2-(3,5-diethylphenyl)acetyl]piperidine hydrochloride hemihydrate, (−) isomer (I), HCl: X=

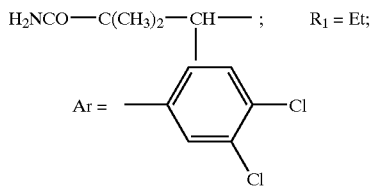

H$_2$NCO—C(CH$_3$)$_2$—CH—; R$_1$ = Et;

Ar = (3,4-dichlorophenyl)

A) 3-(3,4-Dichlorophenyl)-3-(2-hydroxyethyl)-1-[2-(3,5-diethylphenyl)acetyl]piperidine, single isomer 1.15 g of 3,5-diethylphenylacetic acid are added, at RT, to a mixture of 1.64 g of the compound obtained in Preparation 1 in 30 ml of DCM, followed by 3 ml of triethylamine and 3.2 g of BOP, and the mixture is stirred at RT for 2 hours. The reaction mixture is concentrated under vacuum, the residue is taken up in 1N HCl solution and extracted with ether, the organic phase is washed with 1N HCl solution, with water, with 1N NaOH solution, with water, with saturated NaCl solution and dried over Na$_2$SO$_4$, and the solvent is evaporated off under vacuum. The residue is chromatographed on silica gel, eluting with a gradient of a DCM/MeOH mixture from (99/1; v/v) to 95/5; v/v). 1.1 g of the expected product are obtained, which product is used without further processing.

B) 3-(3,4-Dichlorophenyl)-3-(formylmethyl)-1-[2-(3,5-diethylphenyl)acetyl]piperidine, single isomer A solution of 0.5 g of the compound obtained in the above step in 10 ml of DCM is cooled to −78° C., under a nitrogen atmosphere, 0.23 ml of DMSO is added, followed by 0.16 ml of oxalyl chloride, and the mixture is stirred at −78° C. for 30 minutes. 0.95 ml of triethylamine is then added and the mixture is left stirring while allowing it to return to RT. 1N HCl solution is added to the reaction mixture, the resulting mixture is extracted with DCM, the organic phase is washed with 1N HCl solution, with water, with 10% Na$_2$CO$_3$ solution and dried over Na$_2$SO$_4$, and the solvent is evaporated off under vacuum. 0.5 g of the expected product is obtained, which product is used without further processing.

C) 3-[2-[4-(1-Carbamoyl-1-methylethyl)-1-piperidyl]ethyl]-3-(3,4-dichlorophenyl)-1-[2-(3,5-diethylphenyl)acetyl]piperidine hydrochloride hemihydrate, (−) isomer 0.08 ml of acetic acid is added, at RT and under a nitrogen atmosphere, to a solution of 0.23 g of the compound obtained in Preparation 3.1 (free base) in 3 ml of MeOH, followed by a solution of 0.5 g of the compound obtained in the above step in 5 ml of MeOH. After 5 minutes, 0.08 g of sodium cyanoborohydride is added and the mixture is left stirring overnight at RT. The reaction mixture is poured into aqueous 10% NaHCO$_3$ solution and extracted with ether, the organic phase is washed with water and dried over MgSO$_4$, and the solvent is evaporated off under vacuum. The residue is chromatographed on silica H gel, eluting with DCM and then with a gradient of a DCM/MeOH mixture from (99/1; v/v) to (93/7; v/v). The product obtained is dissolved in DCM and acidified to pH=1 by addition of hydrochloric ether, and the solvents are evaporated off under vacuum. 0.51g of the expected product is obtained after trituration from ether, spin-drying and drying.

$\alpha_D^{20}$=−30.5° (c=1; MeOH)

$^1$H NMR: δ (ppm): 0.5 to 2.2:m:23H; 2.2 to 4.65:m:16H; 6.4 to 7.8:m:8H; 9.85:s:1H.

By working according to the procedures described in the above examples, the compounds according to the invention collated in Table I below are prepared.

TABLE I (I) [Structure: X-N(piperazine)-CH₂-CH₂-C(with 3,4-dichlorophenyl)(CH₂CH₂-N-CH₂CH₂ piperidine)-N-C(=O)-CH₂-phenyl-(R₁)₂]

| Example | X | R₁ | Salt, hydrate NMR α$_D^{20}$ (c = 1; MeOH) |
|---|---|---|---|
| 8 (a) | H₂NCO–C(cyclohexyl)–N(CH)(CH₃) | Me | HCl NMR −23.3° |
| 9 (b) | H₂NCO–C(cyclohexyl)–N(CH₃)(CH₃) | Me | 2HCl.1.5 H₂O NMR −26.6° |
| 10 (c) | H₂NCO–C(cyclohexyl)–N(CH)(CH₃) | Cl | HCl.0.5 H₂O NMR −0.4° |
| 11 (d) | H₂NCO–C(Me)(Me)–N(CH₃)(CH₃) | Cl | 2HCl.0.55 H₂O NMR +32° |
| 12 (e) | Me₂N–CO–C(Me)(Me)–N(CH₃)(CH₃) | Cl | 2HCl.1.25 H₂O NMR +2.4° |
| 13 (f) | H₂NCO–C(cyclohexyl)–N(CH₃)(CH₃) | Cl | 2HCl.1.8 H₂O NMR +28.4° |
| 14 (g) | H₂NCO–C(cyclohexyl)–N(CH)(CH₃) | CF₃ | HCl.1.5 H₂O NMR +25.7° |

TABLE I-continued (I) [Structure analogous]

| Example | X | R₁ | Salt, hydrate NMR α$_D^{20}$ (c = 1; MeOH) |
|---|---|---|---|
| 15 (h) | H₂NCO–C(cyclohexyl)–N(CH₃)(CH₃) | CF₃ | 2HCl.1.75 H₂O NMR +25.2° |
| 16 (i) | H₂NCO–C(cyclopropyl)–N(CH)(CH₃) | Me | HCl.1.6 H₂O NMR −24.2° |
| 17 (j) | H₂NCO–C(cyclopropyl)–N(CH)(CH₃) | CF₃ | HCl.1.45 H₂O NMR +28.2° |
| 18 (k) | H₂NCO–C(cyclopropyl)–N(CH)(CH₃) | Cl | HCl NMR +37.2° |
| 19 (l) | H₂NCO–C(Me)(Me)–N(CH₃)(CH₃) | Et | 2HCl.0.65 H₂O NMR −32.8 |
| 20 (m) | O(morpholine)N–CO–C(Me)(Me)–CH(CH₃)₂ | Me | HCl NMR single isomer |

This compound is prepared according to the procedure described in step C of Example 1, starting with the compound obtained in step B of Example 1 and the compound obtained in Preparation 3.5 in the form of the free base.

This compound is prepared according to the procedure described in Example 3, starting with the compound obtained in step B of Example 1 and the compound obtained in Preparation 3.3 in the form of the free base.

This compound is prepared according to the procedure described in step C of Example 4, starting with the compound obtained in step B of Example 4 and the compound obtained in Preparation 3.5 in the form of the free base.

This compound is prepared according to the procedure described in Example 3, starting with the compound obtained in step B of Example 4 and the compound obtained in Preparation 3.2 in the form of the free base.

This compound is prepared according to the procedure described in Example 3, starting with the compound obtained in step B of Example 4 and the compound obtained in Preparation 3.4.

This compound is prepared according to the procedure described in Example 3, starting with the compound obtained in step B of Example 4 and the compound obtained in Preparation 3.3 in the form of the free base.

This compound is prepared according to the procedure described in step C of Example 5, starting with the compound obtained in step B of Example 5 and the compound obtained in Preparation 3.5.

This compound is prepared according to the procedure described in Example 3, starting with the compound obtained in step B of Example 5 and the compound obtained in Preparation 3.3 in the form of the free base.

This compound is prepared according to the procedure described in Example 2, starting with the compound obtained in step B of Example 1 and the compound obtained in Preparation 3.7 in the form of the free base.

This compound is prepared according to the procedure described in step C of Example 5, starting with the compound obtained in step B of Example 5 and the compound obtained in Preparation 3.7.

This compound is prepared according to the procedure described in step C of Example 4, starting with the compound obtained in step B of Example 4 and the compound obtained in Preparation 3.7 in the form of the free base.

This compound is prepared according to the procedure described in step C of Example 7, starting with the compound obtained in step B of Example 7 and the compound obtained in Preparation 3.2 in the form of the free base.

This compound is prepared according to the procedure described in step C of Example 1, starting with the compound obtained in step B of Example 1 and the compound obtained in Preparation 3.8 in the form of the free base.

EXAMPLE 8

$^1$H NMR: δ (ppm): 0.7 to 2.2:m:27H; 2.3 to 4.6:m:14H; 6.4 to 7.7:m:8H; 10.1:s:1H.

EXAMPLE 9

$^1$H NMR: δ (ppm): 0.6 to 2.35:m: 22H; 2.4 to 4.6:m:14H; 6.4 to 8.2:m:8H.

EXAMPLE 10

$^1$H NMR: δ (ppm): 0.7 to 2.25:m:21H; 2.3 to 4.4:m:12H; 6.7 to 7.8:m:8H; 10.1:s:1H.

EXAMPLE 11

$^1$H NMR: δ (ppm): 0.6 to 2.2:m: 12H; 2.3 to 4.4:m:16H; 6.8 to 8.0:m:8H.

EXAMPLE 12

$^1$H NMR: δ (ppm): 0.8 to 2.3:m:12H; 2.35 to 4.4:m:22H; 7.0 to 7.9:m:6H; 10.6:s:1H.

EXAMPLE 13

$^1$H NMR: δ (ppm): 0.9 to 2.3:m:16H; 2.35 to 4.5:m:16H; 7.0 to 7.9:m:8H.

EXAMPLE 14

$^1$H NMR: δ (ppm): 0.9 to 2.3:m:21H; 2.4 to 4.3:m:12H; 6.8 to 8.1:m:8H; 10.0:s:1H.

EXAMPLE 15

$^1$H NMR: δ (ppm): 1.0 to 2.4:m:16H; 2.5 to 4.5:m:16H; 6.9 to 8.1:m:8H; 11.0:bs:1H.

EXAMPLE 16

$^1$H NMR: δ (ppm): 0.4 to 2.3:m:20H; 2.4 to 4.6:m:13H; 6.5 to 7.7:m:8H; 9.6:s:1H.

EXAMPLE 17

$^1$H NMR: δ (ppm): 0.4 to 2.2:m:14H; 2.3 to 4.4:m:13H; 6.5 to 7.8:m:8H; 9.9:s:1H.

EXAMPLE 18

$^1$H NMR: δ (ppm): 0.4 to 2.2:m:14H; 2.3 to 4.4:m:13H; 6.6 to 7.8:m:8H; 9.9:s:1H.

EXAMPLE 19

$^1$H NMR: δ (ppm): 0.6 to 2.6:m: 22H; 2.6 to 4.8:m:16H; 6.5 to 8.0:m:10H.

EXAMPLE 20

$^1$H NMR: δ (ppm): 0.7 to 2.25:m:22H; 2.3 to 4.6:m:21H; 6.4 to 7.7:m:6H; 10.4:s:1H.

EXAMPLE 21

3-[2-[4-(1-Carbamoyl-1-methylethyl)-1-piperidyl]ethyl]-3-(3,4-dimethylphenyl)-1-[2-(3,5-dichlorophenyl)acetyl]piperidine hydrochloride (I), HCl:

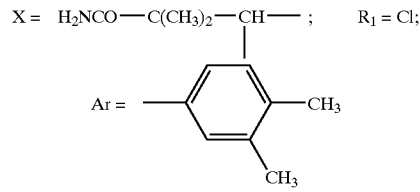

A) 1-[2-(3,5-Dichlorophenyl)acetyl]-3-(3,4-dimethylphenyl)-3-[2-(2-tetrahydropyranyloxy)ethyl]piperidine A mixture of 3 g of the compound obtained in Preparation 1.2, 1.3 g of the compound obtained in Preparation 2.1, 3.2 ml of triethylamine and 4.8 g of BOP in 100 ml of DCM is stirred for 2 hours at RT. The reaction mixture is concentrated under vacuum, the residue is taken up in 1N HCl solution and extracted with EtOAc, the organic phase is washed with water, with 1N NaOH solution, with saturated NaCl solution and dried over $Na_2SO_4$, and the solvent is evaporated off under vacuum. 4.5 g of the expected product are obtained.

B) 1-[2-(3,5-Dichlorophenyl)acetyl]-3-(3,4-dimethylphenyl)-3-(2-hydroxyethyl)piperidine A mixture of 4.5 g of the compound obtained in the above step and 2 ml of concentrated HCl solution in 10 ml of MeOH is stirred for 2 hours at RT. The reaction mixture is concentrated under vacuum, the residue is taken up in MeOH and the solvent is evaporated off under vacuum. The residue is chromatographed on silica gel, eluting with DCM and then with a gradient of a DCM/MeOH mixture from (99/1; v/v) to (95/5; v/v). 3 g of the expected product are obtained.

C) 1-[2-(3,5-Dichlorophenyl)acetyl]-3-(formylmethyl)-3-(3,4-dimethylphenyl)piperidine 10 ml of DCM are cooled to −78° C., 0.5 g of the compound obtained in the above step and 0.18 ml of DMSO are added, under a nitrogen atmosphere, followed by 0.13 ml of oxalyl chloride, and the mixture is left stirring at −78° C. for 30 minutes. 0.75 ml of triethylamine are then added and the mixture is left stirring while allowing it to warm to RT. 1N HCl solution is added to the reaction mixture, the resulting mixture is extracted with DCM, the organic phase is washed with water, with 10% Na$_2$CO$_3$ solution and dried over Na$_2$SO$_4$, and the solvent is evaporated off under vacuum. 0.5 g of the expected product is obtained.

D) 3-[2-[4-(1-Carbamoyl-1-methylethyl)-1-piperidyl]ethyl]-3-(3,4-dimethylphenyl)-1-[2-(3,5-dichlorophenyl)acetyl]piperidine hydrochloride A mixture of 0.5 g of the compound obtained in the above step, 0.35 g of the compound obtained in Preparation 3.1 (free base), 0.1 ml of acetic acid and 0.15 g of sodium cyanoborohydride in 30 ml of MeOH is left stirring overnight at RT. 10% Na$_2$CO$_3$ solution is added to the reaction mixture, the resulting mixture is left stirring for 15 minutes and is extracted with EtOAc, the organic phase is washed with water, with saturated NaCl solution and dried over Na$_2$SO$_4$, and the solvent is evaporated off under vacuum. The residue is chromatographed on silica gel, eluting with DCM and then with a gradient of a DCM/MeOH mixture (99/1; v/v) to (95/5; v/v). The product obtained is dissolved in DCM and acidified to pH=1 by addition of hydrochloric ether, and the precipitate formed is spin-dried. 0.35 g of the expected product is obtained.

$^1$H NMR: δ (ppm): 0.8 to 2.3:m:22H; 2.3 to 4.0:m:13H; 6.5 to 7.6:m:8H; 9.5:s:1H.

EXAMPLE 22

3-[2-[4-(1-Carbamoyl-1-methylethyl)-1-piperazinyl]ethyl]-3-(3,4-dimethylphenyl)-1-[2-(3,5-dichlorophenyl)acetyl]piperidine dihydrochloride, 1 H$_2$O (I), 2HCl:

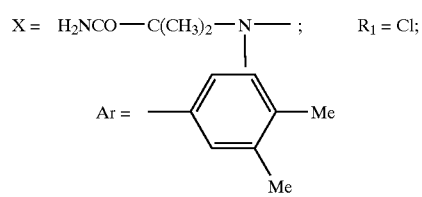

This compound is prepared according to the procedure described in step D of Example 21, starting with the compound obtained in step C of Example 21 and the compound obtained in Preparation 3.2 (free base).

$^1$H NMR: δ (ppm): 1.4; 1s:6H; 2.2: 2s:6H; 1.3 to 4.0:m:26H; 7.0 to 8.0:m:6H.

What is claimed is:

1. A compound of formula (I):

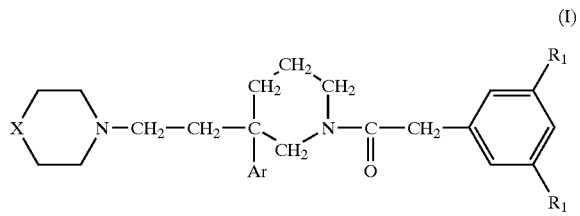

in which:

X represents a group

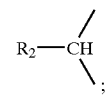

Ar represents a phenyl monosubstituted or disubstituted with a halogen atom; or a (C$_1$–C$_3$)alkyl;

R$_1$ represents a chlorine atom, a bromine atom, a (C$_1$–C$_3$) alkyl or a trifluoromethyl;

R$_2$ represents a group —CR$_3$R$_4$CONR$_5$R$_6$;

R$_3$ and R$_4$ represent the same radical chosen from a methyl, an ethyl, an n-propyl or an n-butyl;

or R$_3$ and R$_4$, together with the carbon atom to which they are attached, constitute a (C$_3$–C$_6$)cycloalkyl;

R$_5$ and R$_6$ each independently represent a hydrogen; a (C$_1$–C$_3$)alkyl;

or R$_5$ and R$_6$, together with the nitrogen atom to which they are attached, constitute a heterocyclic radical chosen from 1-azetidinyl, 1-pyrrolidinyl, 1-piperidyl, 4-morpholinyl, 4-thiomorpholinyl or perhydro-1-azepinyl;

or an acid-addition salt, solvate or hydrate thereof.

2. A compound according to claim 1, in which Ar represents a 3,4-dichlorophenyl or a 3,4-dimethylphenyl.

3. A compound according to claim 1, in which the substituents R$_1$ represent a chlorine atom, a methyl, an ethyl or a trifluoromethyl.

4. A compound according to claim 1 in which R$_3$ and R$_4$ each represent a methyl or, together with the carbon atom to which they are attached, constitute a cyclohexyl or a cyclopropyl.

5. A compound according to claim 1, of formula (I″):

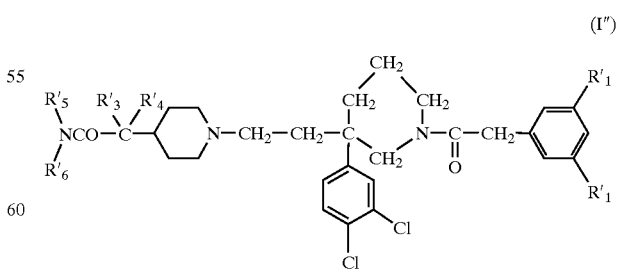

in which:

R′$_1$ represents a chlorine atom, a methyl, an ethyl or a trifluoromethyl;

R'₃ and R'₄ each represent a methyl or, together with the carbon atom to which they are attached, constitute a cyclohexyl or cyclopropyl;

R'₅ and R'₆ each represent hydrogen or a methyl; or an acid-addition salt, solvate or hydrate thereof.

6. A compound according to claim 1 in optically pure form.

7. 3-[2-[4-(1-Carbamoyl-1-methylethyl)-1-piperidyl]ethyl]-3-(3,4-dichlorophenyl)-1-[2-(3,5-dimethylphenyl)acetyl]piperidine, (−) isomer, or an acid-addition salt, solvate or hydrate thereof according to claim 5.

8. 3-[2-[4-(1-N,N-dimethylcarbamoyl-1-methylethyl)-1-piperidyl]ethyl]-3-(3,4-dichlorophenyl)-1-[2-(3,5-dimethylphenyl)acetyl]piperidine, (−) isomer, or an acid-addition salt, solvate or hydrate thereof according to claim 5.

9. 3-[2-[4-(1-Carbamoyl-1-methylethyl)-1-piperidyl]ethyl]-3-(3,4-dichlorophenyl)-1-[2-(3,5-diethylphenyl)acetyl]piperidine, (−) isomer, or an acid-addition salt, solvate or hydrate thereof according to claim 5.

10. 3-[2-[4-(1-Carbamoyl-1-methylethyl)-1-piperidyl]ethyl]-3-(3,4-dichlorophenyl)-1-[2-[3,5-bis(trifluoromethyl)phenyl]acetyl]piperidine, (+) isomer, or an acid-addition salt, solvate or hydrate thereof according to claim 5.

11. A process for preparing a compound according to claim 1 wherein:

1a) a compound of formula (II):

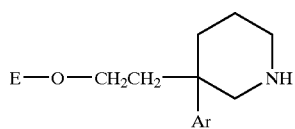

(II)

in which Ar is as defined in claim 1 and E represents hydrogen or an O-protecting group, is treated with a functional derivative of an acid of formula (III):

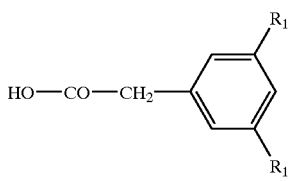

(III)

in which $R_1$ is as defined in claim 1, to give a compound of formula (IV):

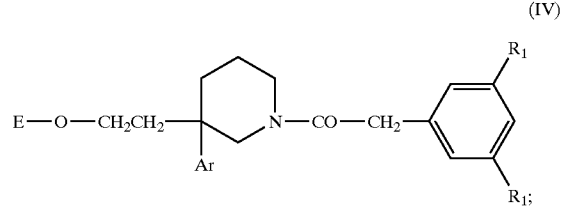

(IV)

2a) when E represents a protecting group, it is removed by the action of an acid or a base, to give the alcohol of the formula:

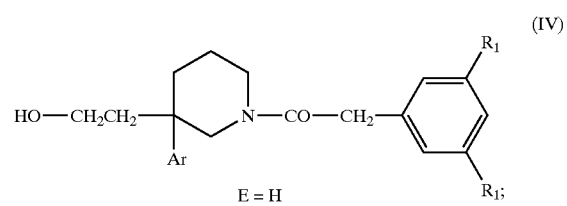

(IV) E=H 3a) the alcohol obtained in step 1a) or in step 2a) of formula (IV, E=H) is treated with a compound of formula (V):

Y—SO₂—Cl (V)

in which Y represents a methyl, phenyl, tolyl or trifluoromethyl group, to give a compound of formula (VI):

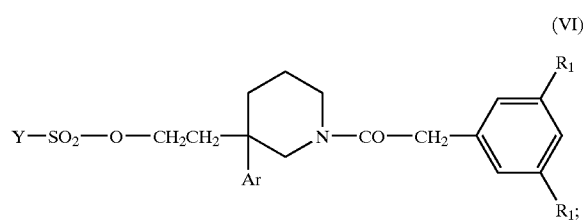

(VI)

4a) the compound of formula (VI) is reacted with a compound of formula (VII):

(VII)

in which X is as defined in claim 1;

5a) and, optionally, the compound thus obtained is converted into an acid-addition salt with an inorganic or organic acid.

12. A pharmaceutical composition comprising a compound according to claim 1 in admixture with a pharmaceutical excipient.

13. A compound according to claim 1 wherein $R_5$ and $R_6$ each represents hydrogen or methyl.

14. A compound according to claim 5 in optically pure form.

15. A pharmaceutical composition comprising a compound according to claim 5 in admixture with a pharmaceutical excipient.

* * * * *